(12) United States Patent
Lee et al.

(10) Patent No.: US 9,649,316 B2
(45) Date of Patent: May 16, 2017

(54) INDUCTION OF TUMOR HYPOXIA FOR CANCER THERAPY

(71) Applicant: Virginia Commonwealth University, Richmond, VA (US)

(72) Inventors: Ruey-min Lee, Ambler, PA (US); Peck-sun Lin, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 154 days.

(21) Appl. No.: 14/043,661

(22) Filed: Oct. 1, 2013

(65) Prior Publication Data

US 2014/0065139 A1 Mar. 6, 2014

Related U.S. Application Data

(62) Division of application No. 12/922,658, filed as application No. PCT/US2009/039899 on Apr. 8, 2009, now Pat. No. 8,591,921.

(60) Provisional application No. 61/043,964, filed on Apr. 10, 2008.

(51) Int. Cl.
| | | |
|---|---|---|
| *A61K 31/53* | (2006.01) | |
| *A61K 31/167* | (2006.01) | |
| *A61K 39/395* | (2006.01) | |
| *C07K 16/22* | (2006.01) | |
| *A61K 31/135* | (2006.01) | |

(52) U.S. Cl.
CPC ............ *A61K 31/53* (2013.01); *A61K 31/135* (2013.01); *A61K 31/167* (2013.01); *A61K 39/3955* (2013.01); *A61K 39/39558* (2013.01); *C07K 16/22* (2013.01)

(58) Field of Classification Search
None
See application file for complete search history.

(56) References Cited

U.S. PATENT DOCUMENTS

| | | | |
|---|---|---|---|
| 3,980,779 | A | 9/1976 | Ley et al. |
| 5,175,287 | A | 12/1992 | Lee et al. |
| 5,202,352 | A | 4/1993 | Okada et al. |
| 5,484,612 | A | 1/1996 | Brown |
| 5,616,584 | A | 4/1997 | Lee et al. |
| 5,624,925 | A | 4/1997 | Lee et al. |
| 5,652,255 | A | 7/1997 | Adams et al. |
| 5,670,502 | A | 9/1997 | Brown |
| 5,849,738 | A | 12/1998 | Lee et al. |
| 6,063,780 | A | 5/2000 | Dexter et al. |
| 6,121,263 | A | 9/2000 | Brown |
| 6,277,835 | B1 | 8/2001 | Brown |
| 6,319,923 | B1 | 11/2001 | Dexter et al. |
| 6,362,184 | B1 | 3/2002 | Lee et al. |
| 6,828,321 | B2 | 12/2004 | Lee et al. |
| 8,591,921 | B2 | 11/2013 | Lee et al. |
| 2003/0185793 | A1 | 10/2003 | Kratz |
| 2006/0160773 | A1 | 7/2006 | Giannini et al. |

FOREIGN PATENT DOCUMENTS

| | | |
|---|---|---|
| JP | H 09-503488 | 4/1997 |
| WO | WO 95/03036 A1 | 2/1995 |
| WO | WO 2004/064734 A2 | 8/2004 |
| WO | WO 2004/075904 A1 | 9/2004 |
| WO | WO 2007/087026 A2 | 8/2007 |

OTHER PUBLICATIONS

Chaplin et al., British J. Cancer (1996) 74, (Suppl. XXVII) S86-S88.*
Zhang et al., Mol. Cancer Ther. 2005;4(10), Oct. 2005.*
Augustin. Translating angiogenesis research into the clinic: the challenges ahead. Br J Radiol. 2003;76 Spec No. 1:S3-10.
Bedikian, et al. Phase II trial of tirapazamine combined with cisplatin in chemotherapy of advanced malignant melanoma. Ann Oncol. Apr. 1997;8(4):363-7.
Bikfalvi, et al. Recent advances in angiogenesis, anti-angiogenesis and vascular targeting. Trends Pharmacol Sci. Dec. 2002;23(12):576-82.
Blum, et al. Hepatocellular carcinoma: an update. Arch Iran Med. Jul. 2007;10(3):361-71.
Brown. SR 4233 (tirapazamine): a new anticancer drug exploiting hypoxia in solid tumours. Br J Cancer. Jun. 1993;67(6):1163-70.
Bruix, et al. Chemoembolization for hepatocellular carcinoma. Gastroenterology. Nov. 2004;127(5 Suppl 1):S179-88.
Cahill, et al. Genotoxic effects of 3-amino-1,2,4-benzotriazine-1,4-dioxide (SR 4233) and nitrogen mustard-N-oxide (nitromin) in Walker carcinoma cells under aerobic and hypoxic conditions. Chem Biol Interact. Mar. 30, 1995;95(1-2):97-107.
Cahill, et al. Metabolism of 3-amino-1,2,4-benzotriazine-1,4-dioxide (SR 4233) by purified DT-diaphorase under aerobic and anaerobic conditions. Biochem Pharmacol. Jan. 26, 1993;45(2):321-9.
Cahill, et al. Reductive activation of N-oxides to cause DNA strand breakage in cell lines in vitro. Biochem Soc Trans. Apr. 1991;19(2):127S.
Cahill, et al. Reductive metabolism of 3-amino-1,2,4-benzotriazine-1,4-dioxide (SR 4233) and the induction of unscheduled DNA synthesis in rat and human derived cell lines. Carcinogenesis. Aug. 1990;11(8):1407-11.
Carmeliet, et al. Angiogenesis in cancer and other diseases. Nature. Sep. 14, 2000;407(6801):249-57.
Cawley, et al. Nitric oxide-evoked transient kinetics of cyclic GMP in vascular smooth muscle cells. Cell Signal. May 2007;19(5):1023-33. Epub Nov. 28, 2006.
Collins, et al. Targeting vascular endothelial growth factor and angiogenesis for the treatment of colorectal cancer. Semin Oncol. Feb. 2005;32(1):61-8.
Costa, et al. In vitro hepatotoxicity of SR 4233 (3-amino-1,2,4-benzotriazine-1,4-dioxide), a hypoxic cytotoxin and potential antitumor agent. Cancer Res. Feb. 15, 1989;49(4):925-9.

(Continued)

*Primary Examiner* — Michael G. Hartley
*Assistant Examiner* — Robert Cabral
(74) *Attorney, Agent, or Firm* — Wilson, Sonsini, Goodrich & Rosati

(57) ABSTRACT

Methods and compositions for enhancing the ability of hypoxia-activated bioreductive agents to kill tumor cells within solid tumors are provided. Local regions of hypoxia are created within a tumor, or within a region containing a tumor, resulting in enhanced activation of hypoxia-activated bioreductive agents (e.g. tirapazamine) within the local region. The activated hypoxia-activated bioreductive agents kill tumor cells in the hypoxic region by catalyzing DNA stand breakage within the tumor cells. Because the activity is localized, side effects that typically occur as a result of systemic administration of bioreductive agents are reduced.

9 Claims, 9 Drawing Sheets

(56) References Cited

OTHER PUBLICATIONS

Covens, et al. A phase II evaluation of tirapazamine plus cisplatin in the treatment of recurrent platinum-sensitive ovarian or primary peritoneal cancer: a Gynecologic Oncology Group study. Gynecol Oncol. Mar. 2006;100(3):586-90. Epub Oct. 24, 2005.
Davis, et al. ZD6126: a novel vascular-targeting agent that causes selective destruction of tumor vasculature. Cancer Res. Dec. 15, 2002;62(24):7247-53.
Del Pozo, et al. Management of hepatocellular carcinoma. Clin Liver Dis. May 2007;11(2):305-21.
Denny, et al. Tirapazamine: a bioreductive anticancer drug that exploits tumour hypoxia. Expert Opin Investig Drugs. Dec. 2000;9(12):2889-901.
Durrant, et al. Development of water soluble derivatives of cis-3, 4', 5-trimethoxy-3'-aminostilbene for optimization and use in cancer therapy. Invest New Drugs. Feb. 2009;27(1):41-52. doi: 10.1007/s10637-008-9139-y. Epub May 31, 2008.
Durrant, et al. Mechanism of cell death induced by cis-3, 4', 5-trimethoxy-3'-aminostilbene in ovarian cancer. Gynecol Oncol. Jul. 2008;110(1):110-7. doi: 10.1016/j.ygyno.2008.02.031. Epub Apr. 22, 2008.
Eberhard, et al. Heterogeneity of angiogenesis and blood vessel maturation in human tumors: implications for antiangiogenic tumor therapies. Cancer Res. Mar. 1, 2000;60(5):1388-93.
Folkman. Angiogenesis. Annu Rev Med. 2006;57:1-18.
Folkman. Antiangiogenesis in cancer therapy—endostatin and its mechanisms of action. Exp Cell Res. Mar. 10, 2006;312(5):594-607. Epub Dec. 22, 2005.
Fong. Mechanisms of adaptive angiogenesis to tissue hypoxia. Angiogenesis. 2008;11(2):121-40. doi: 10.1007/s10456-008-9107-3. Epub Mar. 10, 2008.
Fukumura, et al. Role of nitric oxide in angiogenesis and microcirculation in tumors. Cancer Metastasis Rev. Mar. 1998;17(1):77-89.
Gatzemeier, et al. Tirapazamine-cisplatin: the synergy. Br J Cancer. Jun. 1998;77 Suppl 4:15-7.
Gerber. Anti-angiogenesis: biology is the foundation for therapy. Drug Discov Today. Apr. 15, 2003;8(8):344-6.
Graham, et al. Pharmacokinetics of the hypoxic cell cytotoxic agent tirapazamine and its major bioreductive metabolites in mice and humans: retrospective analysis of a pharmacokinetically guided dose-escalation strategy in a phase I trial. Cancer Chemother Pharmacol. 1997;40(1):1-10.
Hua. New therapy for hypoxic cancer cells: Tirapazamine. Taiwan Cancer Clinic Foundation. Login date Nov. 9, 1995. Accessed: Jul. 10, 2013. http://www.tmn.idv.tw/tcfund/medecine/nm_33.htm. (in Chinese with English translation).
Hwang, et al. Reaction of the hypoxia-selective antitumor agent tirapazamine with a C1'-radical in single-stranded and double-stranded DNA: the drug and its metabolites can serve as surrogates for molecular oxygen in radical-mediated DNA damage reactions. Biochemistry. Oct. 26, 1999;38(43):14248-55.
International search report and written opinion dated Dec. 7, 2009 for PCT Application No. PCT/US2009/39899.
Jain, et al. Effect of vascular normalization by antiangiogenic therapy on interstitial hypertension, peritumor edema, and lymphatic metastasis: insights from a mathematical model. Cancer Res. Mar. 15, 2007;67(6):2729-35.
Jain. Antiangiogenic therapy for cancer: current and emerging concepts. Oncology (Williston Park). Apr. 2005;19(4 Suppl 3):7-16.
Lartigau, et al. Does tirapazamine (SR-4233) have any cytotoxic or sensitizing effect on three human tumour cell lines at clinically relevant partial oxygen pressure? Int J Radiat Biol. Feb. 1995;67(2):211-6. (abstract only).
Ma, et al. Novel agents on the horizon for cancer therapy. CA Cancer J Clin. Mar.-Apr. 2009;59(2):111-37. doi: 10.3322/caac.20003.
Maluf, et al. Phase II study of tirapazamine plus cisplatin in patients with advanced or recurrent cervical cancer. Int J Gynecol Cancer. May-Jun. 2006;16(3):1165-71.
Manukhina, et al. Role of nitric oxide in cardiovascular adaptation to intermittent hypoxia. Exp Biol Med (Maywood). Apr. 2006;231(4):343-65.
Masunaga, et al. Combined effects of tirapazamine and mild hyperthermia on anti-angiogenic agent (TNP-470) treated tumors-reference to the effect on intratumor quiescent cells. Int J Radiat Oncol Biol Phys. Jun. 1, 2000;47(3):799-807.
Masunaga, et al. Dependency of the effect of a vascular disrupting agent on sensitivity to tirapazamine and gamma-ray irradiation upon the timing of its administration and tumor size, with reference to the effect on intratumor quiescent cells. J Cancer Res Clin Oncol. Jan. 2007;133(1):47-55. Epub Aug. 22, 2006.
Maxwell, et al. Activation of the HIF pathway in cancer. Curr Opin Genet Dev. Jun. 2001;11(3):293-9.
McDonald, et al. Imaging of angiogenesis: from microscope to clinic. Nat Med. Jun. 2003;9(6):713-25.
McKeown, et al. Bioreductive drugs: from concept to clinic. Clin Oncol (R Coll Radiol). Aug. 2007;19(6):427-42. Epub May 4, 2007.
Miller, et al. Phase II study of the combination of the novel bioreductive agent, tirapazamine, with cisplatin in patients with advanced non-small-cell lung cancer. Ann Oncol. Dec. 1997;8(12):1269-71.
Neri, et al. Tumour vascular targeting. Nat Rev Cancer. Jun. 2005;5(6):436-46.
Papadopoulou, et al. Potentiation of alkylating agents by NLCQ-1 or TPZ in vitro and in vivo. J Exp Ther Oncol. 2006;5(4):261-72.
Prinz. Recent advances in the field of tubulin polymerization inhibitors. Expert Rev Anticancer Ther. Dec. 2002;2(6):695-708.
Reidy, et al. Therapy for unresectable hepatocellular carcinoma: review of the randomized clinical trials-I: hepatic arterial embolization and embolization-based therapies in unresectable hepatocellular carcinoma. Anticancer Drugs. Jun. 2004;15(5):427-37.
Ruegg, et al. Anti-angiogenic therapies in cancer: achievements and open questions. Bull Cancer. Sep. 2007;94(9):753-62.
Sato. Molecular diagnosis of tumor angiogenesis and anti-angiogenic cancer therapy. Int J Clin Oncol. Aug. 2003;8(4):200-6.
Segreti, et al. Tumor selective antivascular effects of the novel antimitotic compound ABT-751: an in vivo rat regional hemodynamic study. Cancer Chemother Pharmacol. Sep. 2004;54(3):273-81. Epub Jun. 2, 2004.
Senan, et al. Phase I and pharmacokinetic study of tirapazamine (SR 4233) administered every three weeks. Clin Cancer Res. Jan. 1997;3(1):31-8.
Seow, et al. 1,2-Bis(methylsulfonyl)-1-(2-chloroethyl)-2-[[1-(4-nitrophenyl)ethoxy]carbonyl]hydrazine: an anticancer agent targeting hypoxic cells. Proc Natl Acad Sci U S A. Jun. 28, 2005;102(26):9282-7. Epub Jun. 17, 2005.
Shaked, et al. Therapy-induced acute recruitment of circulating endothelial progenitor cells to tumors. Science. Sep. 22, 2006;313(5794):1785-7.
Tozer, et al. Disrupting tumour blood vessels. Nat Rev Cancer. Jun. 2005;5(6):423-35.
Weidner, et al. Tumor angiogenesis and metastasis—correlation in invasive breast carcinoma. N Engl J Med. Jan. 3, 1991;324(1):1-8.
Weidner, et al. Tumor angiogenesis: a new significant and independent prognostic indicator in early-stage breast carcinoma. J Natl Cancer Inst. Dec. 16, 1992;84(24):1875-87.
White, et al. Acute lesions in rats caused by 3-amino-1,2,4-benzotriazine-1,4-dioxide (SR 4233) or nitromin: a comparison with rates of reduction in microsomal systems from target organs. Arch Toxicol. 1992;66(2):100-6.
Willett, et al. Combined vascular endothelial growth factor-targeted therapy and radiotherapy for rectal cancer: theory and clinical practice. Semin Oncol. Oct. 2006;33(5 Suppl 10):S35-40.
Williamson, et al. Phase III trial of paclitaxel plus carboplatin with or without tirapazamine in advanced non-small-cell lung cancer: Southwest Oncology Group Trial S0003. J Clin Oncol. Dec. 20, 2005;23(36):9097-104.
Ziche, et al. Nitric oxide and angiogenesis. J Neurooncol. Oct.-Nov. 2000;50(1-2):139-48.

(56) References Cited

OTHER PUBLICATIONS

Cliffe, et al. Combining bioreductive drugs (SR 4233 or SN 23862) with the vasoactive agents flavone acetic acid or 5,6-dimethylxanthenone acetic acid. Int J Radiat Oncol Biol Phys. May 15, 1994;29(2):373-7.
Durrant, et al. cis-3, 4', 5-Trimethoxy-3'-aminostilbene disrupts tumor vascular perfusion without damaging normal organ perfusion. Cancer Chemother Pharmacol. Jan. 2009;63(2):191-200. doi: 10.1007/s00280-008-0726-6. Epub Mar. 26, 2008.
Emmenegger, et al. Low-dose metronomic daily cyclophosphamide and weekly tirapazamine: a well-tolerated combination regimen with enhanced efficacy that exploits tumor hypoxia. Cancer Res. Feb. 1, 2006;66(3):1664-74.
Masunaga, et al. Combination of the antivascular agent ZD6126 with hypoxic cytotoxin treatment, with reference to the effect on quiescent tumor cells and the dependency on p53 status of tumor cells. Oncol Rep. Aug. 2005;14(2):393-400.
Notice of allowance dated Sep. 4, 2013 for U.S. Appl. No. 12/922,658.
Office action dated Apr. 22, 2013 for U.S. Appl. No. 12/922,658.
Office action dated May 7, 2012 for U.S. Appl. No. 12/922,658.
Office action dated Nov. 7, 2012 for U.S. Appl. No. 12/922,658.
Lencioni, et al., Lipiodol Transarterial Chemoembolization for Hepatocellular Carcinoma: A Systematic Review of Efficacy and Safety Data, Hepatology, 1-77.
Lencioni, et al., Sorafenib or placebo plus TACE with doxorubicin-eluting beads for intermediate stage HCC: The SPACE trial, Journal of Hepatology 2016, 9 pages.

\* cited by examiner control tirapazamine (60 mg/kg)

stilbene 5c (50 mg/kg)

tirapazamine (60 mg/kg) plus stilbene 5c (50 mg/kg)

INDUCTION OF TUMOR HYPOXIA FOR CANCER THERAPY

BACKGROUND OF THE INVENTION

Field of the Invention

The invention generally relates to compositions and methods to increase the ability of hypoxia-activated bioreductive agents to kill tumor cells within solid tumors. In particular, the invention provides methods and compositions to create local regions of hypoxia within a tumor, or within a region containing a tumor, in order to enhance activation of and tumor cell killing by hypoxia-activated bioreductive agents within the local region.

Background of the Invention

Tumor growth requires the development of a network of neovasculature to supply oxygen and nutrients and to remove toxic metabolites. The neovasculature in tumors differ significantly from normal vasculature (1, 2). Tumor neovasculature is abnormal, chaotic and inadequate in structure and function, and some data suggest that tumor vasculature may rely more on tubulin as the cytoskeletal support in contrast to both tubulin and actin as the cytoskeleton in normal tissue (3). Targeting tumor vasculature has evolved into a useful strategy to develop new cancer therapeutics (4). Two approaches are currently used to target tumor vessels. One is to prevent the angiogenic process by blocking angiogenic factors or their receptors in order to prevent new vessel formation. This type of therapy is represented by bevacizumab, a monoclonal antibody against vascular endothelial growth factor (VEGF), and sorafenib or sunitinib, small molecular inhibitors of VEGF receptor tyrosine kinase (4-8).

The second strategy of targeting tumor vasculature is to kill the existing endothelial cells in the tumor directly. This group of compounds is referred to as vascular disrupting agents (VDAs) (9, 10). Their goal is to kill the endothelium of existing tumor vessels to deprive tumors from getting an adequate blood supply, leading to tumor ischemia and eventually tumor necrosis. This group of agents is represented by several small molecules that include combretastatin A4 (CA4), ZD6126, AVE8062, Oxi4503 and stilbene derivatives (9-13). These small molecules kill tumor endothelial cells by interfering with microtubule polymerization at the colchicine site. Several colchicine-site microtubulin inhibitors are currently in development as VDAs.

Induction of Tumor Hypoxia and Development of Compensatory Responses

With both anti-angiogenic agents and vascular disrupting agents, the central theme of these tumor vessel targeting agents is to deprive tumor cells of vascular support so that the tumor develops hypoxia and then undergoes necrosis. Development of hypoxia in a tumor is thus the key requirement to induce tumor cell death. However, hypoxia in tumors is not sufficient to induce cell death because hypoxic tumor cells develop a variety of hypoxia responses such as stabilization of Hypoxia-Induced Factor (HIF) 1-α (14, 15), which induces production of glycolysis enzymes that promote survival in the hypoxic environment, or generation of VEGF and other angiogenic factors to induce angiogenesis. Nitric oxide (NO), another factor that is produced in tumor cells during hypoxia, induces vasodialation and thus also improves tumor blood supply (16, 17). NO is also tightly linked to angiogenesis (18, 19). These compensatory mechanisms can thus result in drug resistance against anti-angiogenic agents and VDAs.

Strategies to Enhance Therapeutic Efficacy

There are a few potential strategies to enhance therapeutic efficacy of targeting tumor vasculature. One is to combine either group of agents with conventional chemotherapy, which is currently a common strategy used with anti-angiogenic agents. Bevacizumab, a monoclonal antibody against VEGF, is typically combined with chemotherapy for treating colorectal cancer, non-small cell lung cancer and breast cancer. VDAs are currently in phase II trials for various solid tumors but none have received FDA approval thus far. One new strategy is to combine anti-angiogenic agents with VDAs. This is based on the observation that VDAs induce elevation of VEGF, which subsequently mobilizes bone marrow endothelial progenitor cells into circulation and is thus responsible for repair of damaged tumor vessels (20). Using an inhibitor of the VEGF pathway could possibly block the mobilization and enhance therapeutic effects (11, 20), but this strategy has not been proved in clinical setting.

Tirapazamine (SR4233; 3-amino-1,2,4-benotriazine-1,4-di-N-oxide) is a bioreductive agent that works exclusively in hypoxic environments and has also been tested as an anti-cancer agent (21). Tirapazamine is activated by cytochrome P450 reductase by a one-electron reaction, thereby generating nitroxide radicals. In the absence of oxygen, nitroxide radicals induce single- and double-strand breaks in DNA to cause cell death. Because of this property, tirapazamine exhibits 15-200-fold greater toxicity to hypoxic cells compared to well-oxygenated cells. This agent has also been shown to be a radiation sensitizer and to act synergistically with platinum compounds in cancer therapy regimens (22, 23).

Mechanism of Action for Tirapazamine

A postulated mechanism of action of tirapazamine is shown in the following figure (24-28). One electron reduction of tirapazamine proceeds through reductive activation by enzymes including cytochrome P-450, NADH-cytochrome P-450 reductase and other flavo- or metalloproteins. The product for the single electron transfer reaction is a free radical (I or II), which can be oxidized by oxygen to yield a superoxide and the parent drug tirapazamine. Alternatively, the free radical (I or II) can acquire a second electron through a hydrogen abstraction reaction intermediate (III) to form a stable mono-N-oxide (SR4317). These divergent fates lead to the selective metabolism of tirapazamine in the hypoxic environment. The acquisition of the second electron from macromolecules was suggested to be the cause of lethal damage to hypoxic cells. Another possible route is the release of a hydroxyl radical from intermediate II to produce SR4317 directly, which can be further metabolized in a similar reaction to SR4330.

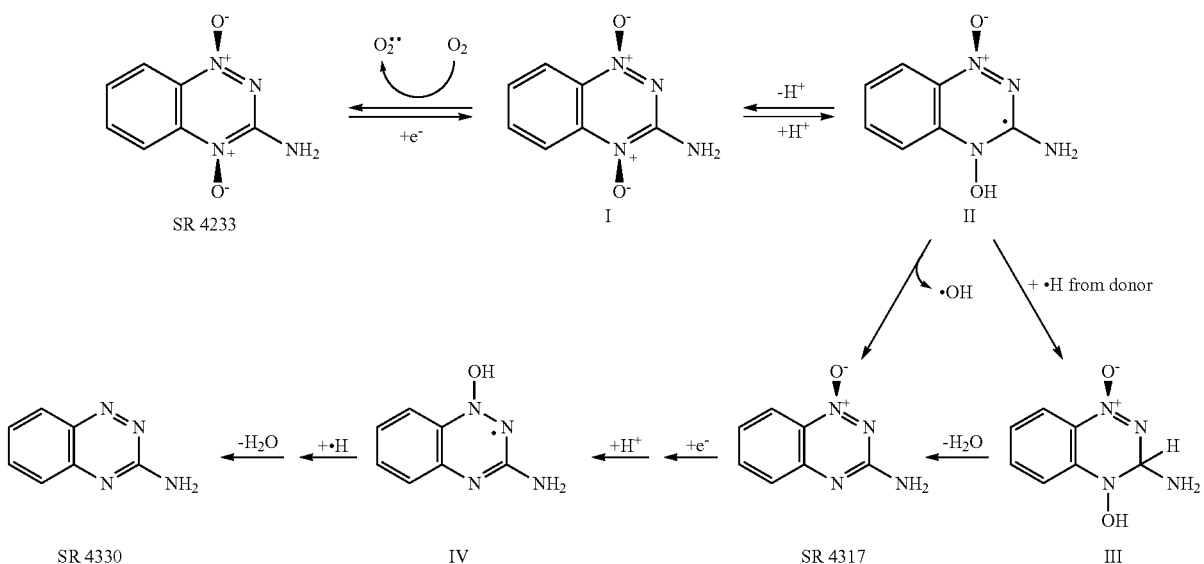

Among all organs, liver is the most important organ for the metabolism of tirapazamine. Costa et al. examined the toxicity of tirapazamine in cultured rat hepatocytes that were transiently incubated in a hypoxic environment at oxygen concentrations of 1, 2, 4, 10 and 20% (29). The dose response curve of tirapazamine to monolayer hepatocytes shifted significantly to the left, meaning more susceptible to death, as the oxygen concentration decreased (P<0.05). The concentration of tirapazamine that caused 50% cell death over 2 h at 4% oxygen was more than 10-fold less than that required at 10% or 20% oxygen concentration. The concentration of tirapazamine required to induce 50% cell death at 2% oxygen was 15-fold less than that required to induce same degree of cell death at 20% oxygen. When the oxygen concentration was further decreased to 1%, the concentration of tirapazamine required for 50% cell death is 50-fold lower than that required at 20% oxygen. These results indicate that the potency of tirapazamine was 15 and 50-fold stronger in 2% and 1% oxygen, respectively, compared with that in 20% normal oxygen environment.

Preclinical and Clinical Development of Tirapazamine

Significant development of tirapazamine has been done both pre-clinically and clinically. Animal studies of tirapazamine showed that its potential side effects include bone marrow toxicity, necrosis of the olfactory nerve, and retinal degeneration (21). A phase I clinical study of tirapazamine by intravenous administration every three weeks showed a maximum tolerated dose (MTD) of 390 mg/m$^2$, and dose limiting toxicities include reversible ototoxicity and transient visual abnormality when the dose was above 330 mg/m$^2$ (30, 31). Other non-specific toxicities included muscle cramps, nausea, vomiting, and diarrhea. Grade 1 thrombocytopenia was noted in one patient receiving 450 mg/m$^2$ and no leucopenia was noted in any patient (30).

Phase II studies of tirapazamine have been carried out for lung cancer, cervical cancer, ovarian cancer, melanoma and head and neck cancer with promising results (32-35). In the phase III randomized study of stage 1V non-small cell lung cancer, 367 patients were randomized to receive carboplatin and paclitaxel with tirapazamine (260 mg/m$^2$ in cycle 1 and increased to 330 mg/m$^2$ in cycles 2-6 if tolerated in cycle 1) (n=181); or carboplatin and paclitaxel with a placebo (n=186). Unfortunately, the result was disappointing in that there was no benefit in response rate, overall survival, or progression free survival in the group that received tirapazamine. In contrast, increased systemic toxicity such as abdominal cramps, fatigue, transient hearing loss, febrile neutropenia, hypotension, myalgias, and skin rash were observed and led to significant drop out from the study (36). The trial was terminated early after interim analysis, which showed that it would not reach the predicted 37.5% improvement in survival. Another large phase III randomized study in pelvis-confined cervical cancer is ongoing for patients receiving cisplatin and radiation with or without tirapazamine, and the result is currently unavailable.

Clearly, there is an ongoing need to provide improved cancer treatments. In particular, it would be beneficial to provide cancer therapy protocols using known agents in a manner that optimizes their efficacy and minimizes deleterious side effects.

SUMMARY OF THE INVENTION

The invention is based on the development of methods and compositions that enhance the anti-tumor activity of hypoxia-activated bioreductive agents (HABAs), while reducing or minimizing the side effects that can occur as a result of systemic administration of such agents. In the presence of oxygen, HABAs are inactive prodrugs; they become activated only under hypoxic conditions. The administration strategies of the invention involve inducing hypoxia at localized regions where it is desirable to activate a HABA, for example, within a tumor or in an area that contains a tumor. When a HABA is also present in the localized hypoxic region, the HABA is activated and exerts its killing effect on cells in the region (e.g. tumor cells), without having a deleterious systemic effect on the organism.

Two general approaches of implementing this technology have been developed. In one approach, the bioreductive agent is administered prior to or concomitant with direct mechanical occlusion of a vessel, i.e. embolization. Embolization can be confined in an isolated, targeted region, resulting in the development of hypoxia in the isolated, targeted region and hence activation of the HABA. In the second approach, a HABA is administered to a tumor in combination with one or more hypoxia-inducing agents such as vascular disrupting agents (VDAs) and anti-angiogenic agents (AAAs). Such agents may also be considered as "chemical embolization" agents as this approach uses VDAs and AAAs (chemical agents) to achieve the purpose of vascular occlusion, in contrast to direct physical occlusion of a vessel using mechanical embolization. However, for the purposes of clarity herein, standard embolizing agents (e.g. Lipiodol) will be considered to be those that are employed only when a mechanical embolization procedure is performed, whereas agents that may be delivered without embolization (VDAs and AAAs) are referred to as "hypoxia-inducing agents". (It is noted that in some embodiments, hypoxia-inducing agents may, optionally, also be delivered during a mechanical embolization procedure.) As is the case for mechanical embolization, local or systemic delivery of agents such as VDAs and AAAs together with a HABA, selectively creates a localized hypoxic environment in a tumor in which the HABA is activated and kills the surrounding tumor cells, but the HABA will remain in the inactive prodrug form in the non-hypoxic region systemically. Thus the deleterious side effects are avoided. In some embodiments of the invention, these methodologies are combined, e.g. AAAs and/or VDAs, and/or direct mechanical embolization, are administered or carried out together with provision of a HABA, so that the selective hypoxic region induced by these approaches can lead to activation of the HABA. The overall effect of these inventive techniques is the rapid, efficacious and synergistic destruction of tumor cells in the localized area, without extensive systemic involvement and deleterious side effects.

It is an object of this invention to use various approaches to induce hypoxia in an isolated region of a tumor or its surrounding area. Such methods include embolization, vascular disrupting agents or anti-angiogenic agents individually or in combination. The process is combined with administration of a hypoxia-activated bioreductive agent, which is activated exclusively in the hypoxic region to induce tumor cell death. Systemic toxicities will also be minimized to gain the maximal benefit.

The invention thus provides a method of selectively killing tumor cells in an animal. The method comprises the steps of: 1) providing the animal with a hypoxia-activated bioreductive agent; and 2) locally forming, within a tumor or a defined area containing one or more tumors, a region of hypoxia of 10% or lower oxygen. The hypoxia activated bioreductive agent becomes activated for killing tumor cells at the region of hypoxia within the tumor or defined area. In one embodiment, the step of locally forming the region of hypoxia is achieved by providing the animal with one or more of vascular disrupting agents and anti-angiogenic agents (i.e. with one or more vascular disrupting agents or with one or more anti-angiogenic agents, or a combination of one or more vascular disrupting agents and one or more anti-angiogenic agents). In some embodiments, the step of providing the animal with one or more of vascular disrupting agents and anti-angiogenic agents is performed systemically. In other embodiments, the step of providing the animal with one or more of vascular disrupting agents and anti-angiogenic agents is performed locally at the region. In yet other embodiments, the step of locally forming the region of hypoxia is performed after the step of providing. Alternatively, the step of locally forming the region of hypoxia may be performed simultaneously with the step of providing. In some embodiments of the invention, the locally forming step provides one or more vascular disrupting agents selected from combretastatin, combretastatin derivatives, (5S)-5-(acetylamino)-9,10,11-trimethoxy-6,7-dihydro-5H-dibenzo[a,c]cyclohepten-3-yl dihydrogenphosphate (ZD6126), DMXAA (5,6-dimethylxanthenone-4-acetic acid, (N-[2-[4-hydroxyphenyl)amino]-3-pyridinyl]-4-methoxybenzenesulfonamide) (E7010 or ABT-751), stilbene derivatives such as cis-3,4',5-trimethoxy-3'-aminostilbene (stilbene 5c) and cis-3,4',5-trimethoxy-3'-hydroxystilbene (stilbene 6c) or their derivatives, and a prodrug morpholino-carbamate derivative of stilbene 5c. In the same or other embodiments, the locally forming step provides one or more anti-angiogenic agents selected from bevacizumab, sorafenib, sunitinib, aflibercept, IMC-1C11, vatalanib (PTK-87), N-(2,3-dihydro-3,3-dimethyl-1H-indol-6-yl)-2-[(4-pyridinylmethyl)amino]-3-pyridinecarboxamide (AMG 706), 3-(4-Bromo-2,6-difluoro-benzyloxy)-5-[3-(4-pyrrolidin-1-yl-butyl)-ureido]-isothiazole-4-carboxylic acid amide (CP-547,632), pazopanib (GW-786034), N-(4-(3-amino-1H-indazol-4-yl)phenyl)-N'-(2-fluoro-5-methylphenyl)urea (ABT-869), and cediranib (AXD-2171). In some embodiments, the hypoxia activated bioreductive agent is tirapazamine, and the locally forming step includes the step of providing cis-3,4',5-trimethoxy-3'-aminostilbene (stilbene 5c). In yet other embodiments, the locally forming step includes providing bevacizumab. When both vascular disrupting and anti-angiogenic agents are administered, the step of locally forming may include the steps of administering one or more vascular disrupting agents followed by administering one or more anti-angiogenic agents.

In other embodiments of the invention, the step of locally forming the region of hypoxia is performed by embolization. Embolization may include the step of administering one or more embolizing agents. In some embodiments, the step of providing is performed prior to said step of locally forming. In other embodiments, the step of providing is performed simultaneously with the step of locally forming. In this embodiment of the invention, the hypoxia activated bioreductive agents may be tirapazamine, banoxantrone (AQ4N), porfitomycin, apaziquone (EO9), 1,2-bis(methylsulfonyl)-1-(2-chloroethyl)-2-[[1-(4-nitrophenyl)ethoxy]carbonyl]hydrazine (KS 119), dinitrobenzamide mustard derivative (such as PR 104) or 4-[3-(2-nitro-1-imidazolyl)-propylamino]-7-chloroquinoline hydrochloride (NLCQ-1, NSC 709257).

In some embodiments of the invention, the region is located in the liver of said animal. In some embodiments of the invention, a level of oxygen in said region of hypoxia is 5% or lower. In some embodiments of the invention, the step of providing is performed locally, whereas in other embodiments, the step of providing is performed systemically.

The invention also comprises a composition or kit for selectively killing tumor cells in an animal. The composition or kit comprises 1) tirapazamine, and 2) one or more of anti-angiogenic agents and vascular disrupting agents. The one or more of anti-angiogenic agents and vascular disrupting agents are selected from bevacizumab, sorfenib, sunitinib aflibercept, IMC-IC11, vatalanib, N-(2,3-dihydro-3,3-dimethyl-1H-indol-6-yl)-2-[(4-pyridinylmethyl)amino]-3-pyridinecarboxamide (AMG 706), 3-(4-Bromo-2,6-difluoro-benzyloxy)-5-[3-(4-pyrrolidin-1-yl-butyl)-ureido]-isothiazole-4-carboxylic acid amide (CP-547,632), pazopanib (GW-786034), N-(4-(3-amino-1H-indazol-4-yl)phenyl)-N'-(2-fluoro-5-methylphenyl)urea (ABT-869), and cediranib (AXD-2171), combretastatin, combretastatin derivatives, (5S)-5-(acetylamino)-9,10,11-trimethoxy-6,7-dihydro-5H-dibenzo[a,c]cyclohepten-3-yl dihydrogenphosphate (ZD6126), DMXAA (5,6-dimethylxanthenone-4-acetic acid, (N-[2-[4-hydroxyphenyl)amino]-3-pyridinyl]-4-methoxybenzenesulfonamide) (E7010 or ABT-751), stilbene derivatives such as cis-3,4',5-trimethoxy-3'-aminostilbene (stilbene 5c) and cis-3,4',5-trimethoxy-3'-hydroxystilbene (stilbene 6c) or their derivatives, and prodrugs such as morpholino-carbamate derivatives of stilbene 5c. In one embodiment, the one or more of anti-angiogenic agents and vascular disrupting agents includes cis-3,4',5-trimethoxy-3'-aminostilbene (stilbene 5c). In another embodiment, the one or more of anti-angiogenic agents and vascular disrupting agents includes bevacizumab

DETAILED DESCRIPTION

Figure 1A:
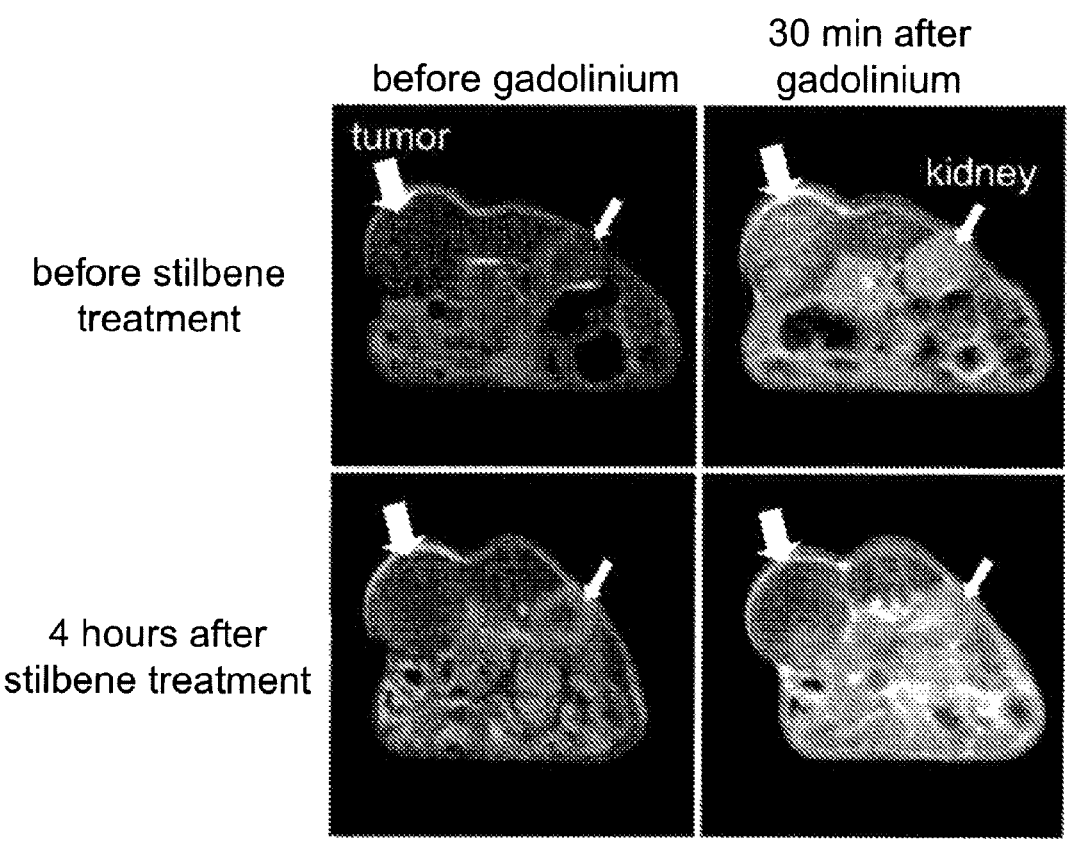
FIGS. 1A and B. Study of tumor perfusion using accumulation of gadolinium at 30 min after gadolinium injection. (A) T1-weighted images before and after stilbene 5c treatment in the same mouse. Nude mice with established subcutaneously UCI101 tumor xenografts were analyzed with DCE-MRI for tumor perfusion. DCE-MRI images were collected for 30 min after injection of gadolinium (OmniScan) into tail veins. The same mice were studied before and after stilbene 5c treatment to avoid individual variation. The left panels show the T1-weighted images before injection of gadolinium. The right panels show images at 30 min after injection of gadolinium. The upper panels show gadolinium enhancement in tumor and kidney before mice were treated with stilbene 5c. The lower panels show that kidney enhancement remained the same, similar to the condition before stilbene treatment. However, stilbene 5c treatment dramatically decreased tumor enhancement by gadolinium (right lower panel) compared with the right upper panel before stilbene treatment. The tumor is marked with a large arrowhead and the kidney with a small arrowhead in each image. Shown are the representative images of one of 6 mice that were studied. (B) Average of calculated gadolinium concentrations in tumor and muscle before and after stilbene 5c treatment. The same experiments were performed in six mice for statistical analysis. For calculation of tissue gadolinium concentration to represent the tissue perfusion, T1 map before and 30 min after gadolinium injection was generated. Tumors signals decreased to 62.8% on average after stilbene 5c treatment; whereas muscle shows no significant change after stilbene treatment.

The present invention provides new, synergistic treatment combinations to kill solid tumor cancer cells, and methods of using the new treatment combinations to treat malignant or cancerous solid tumors. The new combinations locally enhance the anti-tumor activity of hypoxia-activated bioreductive agents (HABAs) such as tirapazamine, while reducing or minimizing the side effects that heretofore have occurred as a result of the systemic administration of HABAs. In the presence of oxygen, the bioreductive agent is an inactive prodrug; conversion to an active form occurs under conditions of low oxygen (hypoxia). According to the invention, active forms of the bioreductive agents are advantageously confined to a desired area of action, e.g. within a tumor or in a circumscribed, defined area that includes one or more tumors. Two general approaches have been developed, both of which involve the creation of a localized hypoxic region within which the bioreductive agent is activated. In one approach, this is accomplished by mechanical embolization of one or more blood vessels that supply the targeted region, usually by administration of embolizing agents through a catheter placed by interventional radiologists to occlude the vessel mechanically. In the second approach, one or more hypoxia-inducing agents such as vascular disrupting agents (VDAs and/or) anti-angiogenic agents (AAAs) are administered locally or systemically to create a localized hypoxic region within which a co-administered HABA is activated. Various combinations of these methods are also contemplated (e.g. embolization plus one or more hypoxia-inducing agents), the overall effect being targeted, localized provision of an activated bioreductive agent, and efficacious killing of tumor cells within or at the targeted site without the side effects usually caused by systemic exposure to bioreductive agents. This enhancement may also permit the use of lower doses of the agents while maintaining an adequate and efficacious level of tumor cell killing, thereby further decreasing toxicity.

By "region of hypoxia" we mean that the level of oxygen within the region is at least lower or less than about 10%, and preferably lower or less than about 5%. For example, the level of oxygen in the hypoxic region may be about 10, 9, 8, 7, 6, 5, 4, 3, 2, or 1%. Generally, an oxygen level of about 10% or lower, and preferably about 5% or lower, is sufficient to activate hypoxia-activated bioreductive agents such as tirapazamine to a level that is at least 10-fold more active than the prodrug form. Those of skill in the art are familiar with the measurement of oxygen levels in biological systems, and are also aware that oxygen measurements may be expressed in "mm Hg", wherein, for example, 10% $O_2$ is equal to 76 mmHg and 1% $O_2$ is equal to 7.6 mmHg.

Those of skill in the art will recognize that several hypoxia-activated bioreductive agents exist that can be used in the present invention, examples of which include but are not limited to tirapazamine, banoxantrone (AQ4N), porfiromycin, apaziquone (EO9), 1,2-bis(methylsulfonyl)-1-(2-chloroethyl)-2-[[1-(4-nitrophenyl)ethoxy]carbonyl]hydrazine (KS 119), dinitrobenzamide mustard derivative (such as PR 104) and 4-[3-(2-nitro-1-imidazolyl)-propylamino]-7-chloroquinoline hydrochloride (NLCQ-1, NSC 709257) (37-39).

By "enhancing" or "increasing" the activity of a hypoxia-activated bioreductive agent, we mean that, when a given quantity of a hypoxia-activated bioreductive agent is administered to a solid tumor, or an area containing a solid tumor, the level of tumor cell death within the solid tumor is greater when administration is carried out according to the methods described herein (i.e. when local regions of hypoxia are generated in the tumor, or in an area that contains the tumor, by the methods described herein), than when the same amount of a hypoxia-activated bioreductive agent is administered to a solid tumor, or an area containing a solid tumor, but regions of hypoxia are not generated by the methods described herein. Generally, the increase in activity is at least about 10 fold, or greater, and the increase may be much higher e.g. from about 20-200 fold, or from about 50 to 200 fold, or 100 to 200 fold.

In one embodiment of the invention, the classic and most clinically advanced bioreductive agent tirapazamine, or one or more derivatives thereof, is utilized in the practice of the invention. Tirapazamine has thus far failed in clinical development. In phase I and phase II trials, tirapazamine by itself was tolerated in doses up to 390 mg/m$^2$. A detailed examination of the failed phase III clinical trials shows that tirapazamine was combined with chemotherapeutic agents such as carboplatin and paclitaxel (36). The assumption was that the treated tumors had both well perfused areas and poorly perfused areas, and that traditional chemotherapy (carboplatin/paclitaxel) would work in well-perfused area whereas tirapazamine would have a cytotoxic effect in the poorly perfused hypoxic regions. However, an enhanced cytotoxic effect between platinum compounds and tirapazamine was detected in both oxygenated and hypoxic environments (36), although the effect was greater in hypoxic cells. The amount of drug that was actually delivered to the hypoxic tumor in each patient is completely unknown. The trial thus subjected the enrolled patients to unnecessary exposure to tirapazamine through systemic administration, which then resulted in general systemic toxicity. The trial also adopted the standard approach of increasing the dose of tirapazamine to a level close to its maximally tolerated dose, and hence created the problems of non-specific toxicity such as neutropenia, hypotension, fatigue, neuropathy, hearing loss etc. The systemic distribution of the chemotherapy-tirapazamine combination explains the enhanced systemic side effects of this combination.

Keeping these results in mind, and based on the fact that tirapazamine has an enhanced activity of about 15-200 fold greater cytotoxicity in hypoxic cells compared to well-oxygenated cells, the present invention provides novel approaches to improve the efficacy of tirapazamine while minimizing adverse side effects that have up to now been observed.

Embolization

By "embolization" we mean a localized therapy used in a tumor or a region containing tumor that is supplied by an identifiable arterial branch, for example, a hepatic artery that supplies a hepatocellular carcinoma, by injecting materials (Lipiodol, gelfoam, blood clot, etc.) to induce occlusion of the branch of the artery supplying the region containing the tumor so that the tumor cells cannot obtain adequate blood flow and die. The anatomy of the blood supply of the region and the surrounding normal organs or tissues determines whether the surrounding organs/tissues may experience significant damage due to lack of blood supply after embolization. For example, normal liver is supplied by dual vessels, the hepatic artery and the portal vein, and thus allows the occlusion of the hepatic artery or a branch of it without the consequence of significant damage to normal liver. This procedure is generally performed by interventional radiologists, who place a catheter from the femoral artery in the groin and advance the tip of the catheter to the branch of the hepatic artery that supplies the tumor under fluoroscope X-ray guidance. Once the arterial branch supplying tumor is identified by injection of contrast material, embolizing agents such as Lipiodol or gelfoam, are injected to occlude the branch. This procedure is a standard loco-regional therapy for the treatment of hepatocellular carcinoma (40-43).

In one embodiment of the invention, a hypoxia-activated bioreductive agent (HABA) such as tirapazamine is combined with embolization for the treatment of tumors in localized areas. Without being bound by theory, there are three rationales for this approach. First, embolization provides a hypoxic tumor environment to enhance the effect of tirapazamine. Second, administration of tirapazamine with embolization limits the distribution of tirapazamine to the region that is supplied by the embolized vessel. Third, because the embolization-induced hypoxic effect is limited to the tissue that is supplied by the vessel that is embolized, no systemic hypoxia is induced and systemic toxicity due to activated tirapazamine is thus avoided. In one embodiment of this aspect of the invention, tirapazamine is mixed or dissolved in an agent commonly used for standard embolization such as Lipiodol. As a result of the co-administration of the two agents, tirapazamine is trapped within the tumor along with the embolizing agent such as Lipiodol. This results in a sustained release of activated tirapazamine into the hypoxic tumor and a cytotoxic effect ensues. Once tirapazamine is released from the embolized region, it is quickly metabolized within the liver and inactivated. Therefore, systemic toxicity of tirapazamine is minimized. This unique combination thus has the significant advantage of fully exploiting the cell-killing capability of tirapazamine and completely eliminates the problem of systemic toxicity observed in the previous clinical studies (36), in which tirapazamine was administered intravenously along with conventional chemotherapy.

Lipiodol is the most frequently used embolizing agent. Other embolizing agents that may be used in the practice of the invention include but are not limited to gelform, blood clots, nanoparticles or any clinically proven mechanical agent that can achieve the purpose of vascular occlusion. The administration of embolizing agents and a hypoxia-activated bioreductive agent (HABA) can be carried out in any suitable manner. For example, the HABA may be administered prior to administration of the embolizing agent (e.g. from about 1-120 minutes before), and subsequent administration of the embolizing agent "traps" the HABA in the region. Alternatively, the two agents may be administered together (e.g. using a preparation that includes the two agents in a mixture). In general, the dosage of HABA that is administered will be in the range of from about 1 mg to about 200 mg (e.g. of tirapazamine), and preferably from about 5 to about 50 mg, for a patient being treated by this method; and the dose of embolizing agent that will be administered will be in the range of from about 5-40 ml, and preferably from about 20-30 ml of e.g. Lipiodol. Sufficient embolizing agent is administered to achieve complete occlusion of the intended branch of the vessel under fluoroscope X-ray examination, to ensure the creation of a hypoxic region or condition in the embolized area. Administration of the embolizing agent is usually carried out by intra-arterial injection. Alternatively, embolization may be carried out by other means such as particular beads to induce occlusion.

Types of cancers that can be treated by this method include any that occur in positions within the body which can be isolated via embolization, for example, hepatocellular (liver) carcinoma, cholangiocarcinoma, and metastatic cancer from colon or other gastrointestinal organs. This strategy can be used for any cancer which can be treated by embolization, or for any tumor that is located within an area of the body that can be embolized without unduly harming the patient, such as sarcoma of the limbs. In particular, this technique is used in the treatment of hepatocellular carcinoma as this type of cancer is routinely treated by embolization. Chemotherapy is also commonly administered, called chemoembolization, in which chemotherapy is administered simultaneously with embolizing agents to trap chemotherapy agents exclusively in the embolized region to minimize the systemic toxicity and enhance therapeutic benefit. Also, in most instances the mechanical embolization in not permanent, and the duration of vascular occlusion can be controlled by the proper selection of embolizing agents, permitting the activated HABA to work for a period of time to execute the effect of tumor killing, and then to be inactivated by an influx of oxygen into the area when the blood flow in the region recovers. The effect of mechanical embolization plus administration of a BABA is synergistic with respect to tumor cell killing, in that the level of tumor cell killing that occurs with this combination therapy is greater than would be expected, based on when each method is used alone, i.e. the effect is not merely additive.

There are several advantages of using e.g. tirapazamine with embolization or chemoembolization for the treatment of, for example, hepatocellular carcinoma. Among all the human malignancies, tirapazamine is particularly useful for hepatocellular carcinoma or primary liver cancer when it is administered by intrahepatic artery injection along with embolization. One reason is that tirapazamine requires P450 for activation, and P450 is abundant in liver. Second, tirapazamine works under hypoxic conditions, which are induced by embolization of the feeding hepatic artery. Tirapazamine is trapped in the liver and is then slowly released into the hepatocellular carcinoma. After embolization, tirapazamine will be metabolized in the liver quickly, thereby avoiding spill-over to other normal organs and minimizing systemic toxicity. In addition, if combined with VDAs (as described below), the relative specificity of VDAs to tumor vessels and enhancement of the effect of embolization will also help to minimize systemic toxicity.

Combining Hypoxia-Activated Bioreductive Agents with Vascular Disrupting agents (VDAs)

In other embodiments of the invention, a hypoxia-activated bioreductive agent is used in conjunction with a VDA that induces hypoxia. VDAs that may be used in the practice of the invention include but are not limited to: the combretastatin derivatives (9), (5S)-5-(acetylamino)-9,10,11-trimethoxy-6,7-dihydro-5H-dibenzo[a,c]cyclohepten-3-yl dihydrogenphosphate (ZD6126) (44), DMXAA (5,6-dimethylxanthenone-4-acetic acid (9), (N-[2-[4-hydroxyphenyl) amino]-3-pyridinyl]-4-methoxybenzenesulfonamide) (E7010 or ABT-751) (45), stilbene derivatives such as cis-3,4',5-trimethoxy-3'-aminostilbene (stilbene 5c) and cis-3,4',5-trimethoxy-3'-hydroxystilbene (stilbene 6c) or their derivatives and prodrugs (morpholino-carbamate derivative of stilbene 5c) described, for example, by U.S. patent application Ser. No. 11/738,813 (Lee, et al., the complete contents of which is herein incorporated by reference). These compounds induce profound hypoxia selectively in tumors even if administered systemically (20). The administration of VDAs may be considered a type of chemical embolization, which is to use a chemical agent to achieve the same goal of embolization selectively in a tumor containing region in contrast to the direct occlusion of a vessel in standard embolization described above. Combinations of VDAs and hypoxia-activated bioreductive agents such as tirapazamine are surprisingly more effective than would be predicted based on the activity of either agent alone in the treatment of solid tumor malignancies, i.e. their activity is synergistic (the tumor killing effect of the combined agents is greater than the arithmetic sum of the effect of each agent alone). For example, VDAs given after tirapazamine allow activation of tirapazamine and increase subsequent tumor cell killing by at least 10 fold or higher, compared to the level of tumor cell killing by either agent alone. This strategy may also be combined with embolization described earlier to be even more effective in inducing tumor hypoxia and tirapazamine activation.

By a "synergistic" interaction or effect, we mean that the effect of administering two (or more) agents or treatment modalities together is greater than the simple additive effect that would be expected if each agent exerted its effect independently. In other words, the agents interact in some manner that increases the total effect that is observed beyond what would be expected. For example, the administration of a tirapazamine alone to a solid tumor typically results in a level of tumor cell death of about 10-20%. The administration of a VDA alone to a solid tumor typically results in a level of tumor cell death of about 10-20% as well. However, when the two are administered together, the level of tumor cell killing is nearly 70-80%, which is greater than the simple arithmetic sum of the two levels achieved by tirapazamine alone and the VDA alone. If the effect was additive, a maximum of about 20-40% would be predicted. The level of 70-80% is thus at least about 2-4 fold higher than the maximum that would be expected if no synergism was observed. According to the present invention, synergy is observed when an HABA is administered in conjunction with the creation of localized hypoxic regions by 1) embolism, 2) administration of an AAA, or 3) administration of a VDA, or some combination of two or more of these three. The level of synergy is generally at least about 2-5 fold higher (e.g. 2, 3, 4, or 5 fold higher) than would be predicted, and may be even greater (e.g. 6-10 fold or more).

Representative levels of synergy that are observed are shown in Example 5 (FIG. 5), in which either tirapazamine or stilbene 5c, a VDA, induces 10-20% tumor necrosis alone; whereas combination of tirapazamine and stilbene 5c induces tumor necrosis increases to 70-80%. The distribution of necrosis is also mainly in the center of the tumor, which is consistent with the notion that tumor necrosis is due to suppression of tumor blood flow and induction of hypoxia, as the tumor in the peripheral region can obtain some oxygen support by diffusion from the surrounding normal tissue.

The combination of tirapazamine and ZD6126 has been studied by Masunaga et al. (46). However, the sequence of administration described by Masunaga et al. differs from that which is described herein. Masunaga et al. administered ZD6126 to mice by intraperitoneal injection first, and tirapazamine was given 1 and 24 hours afterwards. Data provided in the Examples section below demonstrates that VDAs induce tumor vascular shut down immediately (e.g. within minutes) of administration. Thus, administering tirapazamine after ZD6126 is an incorrect sequence because tirapazamine will not be delivered to the tumor once tumor blood flow is suppressed by ZD6126. Instead, tirapazamine should be delivered to the tumor before VDAs are administered to allow distribution of tirapazamine into tumor. It is likely that administration in the reverse order described by Masunaga et al. significantly compromises therapeutic efficacy due to failure of delivery of tirapazamine to the tumor. Under this reverse order, tirapazamine would be mainly distributed to non-tumorous tissue as tumor blood flow is selectively suppressed after administration of ZD6126, which not only compromises the therapeutic benefit of tirapazamine, but also potentially increases systemic toxicities. The method of the present invention thus provides a key advantage compared with that of Masunaga et al., as described in the Examples section below, and illustrated in FIG. 3, in which tumor blood flow and hypoxia could develop within minutes after administration of a VDA.

In this embodiment of the invention, the dose of HABA that will be administered will be in the range of from about 100 to about 300 mg/m$^2$ if tirapazamine is administered systemically, and preferably from about 150 to about 250 mg/m$^2$, and the dose of VDA that will be administered will be in the range of from about 10 mg/m$^2$ to about 100 mg/m$^2$, and preferably from about 50 to about 100 mg/m$^2$ depending on the dose proven to be effective in suppressing tumor blood flow in the clinical trials. The amount of VDA that is administered is sufficient to cause the level of oxygen in the region to decrease to below about 10%, or preferably below about 5%, a level of oxygen that increases the activity of HABAs by at least 10 fold.

Methods of administering VDAs include but are not limited to intravenous, intraperitoneally, intramuscular, subcutaneous, intra-arterial, direct intratumor injection and oral administration.

Combining Hypoxia-Activated Bioreductive Agents with Anti-angiogenic agents (AAAs)

In yet another embodiment of the invention, one or more HABAs are combined with AAAs such as, for example, a vascular endothelial growth factor (VEGF) monoclonal antibody (such as bevacizumab) or inhibitors of VEGF receptor tyrosine kinase (such as sorafenib or sunitinib). Co-administration causes synergism between the effects of AAAs and the HABA by prolonging the duration of tumor hypoxia, and further enhances the therapeutic effect of the HABA.

AAAs that may be used in the practice of the invention include but are not limited to: bevacizumab, sorafenib, sunitinib, aflibercept, IMC-1C11, vatalanib (PTK-87), N-(2, 3-dihydro-3,3-dimethyl-1H-indol-6-yl)-2-[(4-pyridinylmethyl)amino]-3-pyridinecarboxamide (AMG 706), 3-(4-Bromo-2,6-difluoro-benzyloxy)-5-[3-(4-pyrrolidin-1-yl-butyl)-ureido]-isothiazole-4-carboxylic acid amide (CP-547,632), pazopanib (GW-786034), N-(4-(3-amino-1H-indazol-4-yl)phenyl)-N'-(2-fluoro-5-methylphenyl)urea (ABT-869), and cediranib (AXD-2171) (47).

In this embodiment of the invention, the dose of HABA that will be administered will be in the range of from range of from about 100 to about 300 mg/m$^2$ if tirapazamine is administered systemically, and preferably from about 150 to about 250 mg/m$^2$, and the dose of AAA that will be administered will be in the range of from about 5 to 15 mg/kg for bevacizumab, and about 200-400 mg orally twice a day for sorafenib. For other agents, the dosage may vary depending on potency of the agent used. The amount of AAA that is administered is sufficient to cause the level of oxygen in the region to decrease to below about 10%, and preferably below about 5%, i.e. to create a hypoxic region.

The application of AAA to induce tumor hypoxia in combination with HABAs is characterized by two critical factors. The first is the half-life of the AAAs. Monoclonal antibodies such as bevacizumab have a half-life of over 7 days and work by neutralization of the angiogenic factor VEGF. The deprivation of VEGF eventually prevents new vessel formation in tumors and results in tumor hypoxia due to the consumption of oxygen within the tumor (48-50). Small molecular compounds such as sorafenib and sunitinib have half lives of less than 24 hours and work by directly inhibiting the kinase activity of VEGF receptors. Therefore the timing of induction of hypoxia by AAAs can be difficult to control even when the drug half life is known. The situation is in contrast to application of VDAs, in which tumor vessels are immediately shut down within minutes and hypoxia develops almost immediately (Example 3). With the half-life of tirapazamine being about 40 min in humans, the timing of co-administration of tirapazamine relative to the administration of AAAs is challenging. Second, AAAs can also induce temporary normalization of tumor vasculature (51-53) and actually improve tumor blood flow and oxygen level in the tumor. This theory was used to explain the rationale of combining AAAs with radiation, in which adequate oxygenation is essential for tumor killing by radiation whereas hypoxia compromises the radiation effect (51). This effect of temporary normalization of tumor vasculature by AAAs is counterintuitive to the desired hypoxic environment for activation of tirapazamine or other HABAs. Hence the application of HABAs with AAA alone is expected to be challenging. The invention thus proposes to combine VDAs and AAAs as an approach to induced tumor hypoxia. The rationale is to use VDAs to induce immediate suppression of tumor blood flow to induce hypoxia and activation of HABAs. However, with induction of tumor hypoxia, the tumor will develop compensatory hypoxic responses, such as production of VEGF or other angiogenic factors to mobilize endothelial progenitor cells from bone marrow to repair the damaged tumor vasculature (20). Combination of VDAs with AAAs such as bevacizumab helps to prevent the compensatory effect of VEGF and inhibit the repair process in tumor vessels to enhance the effect of VDAs in causing the tumor to remain in the hypoxic state (20). The synergistic effect between stilbene VDAs and bevacizumab is shown in Example 4.

Thus, the components of the combination tumor therapies described herein include one or more anti-angiogenic agents (AAAs), and one or more vascular disrupting agents (VDAs), and a hypoxia-activated bio-reductive agent (HABA). The combination of AAAs and VDAs induce prolonged hypoxia in tumor cells when administered together, and display some efficacy in killing tumor cells on their own, but these agents administered alone have been relatively ineffective in treating solid tumors. However, their activity is significantly enhanced in a synergistic (non-additive) manner when they are administered as described herein in combination with hypoxia-activated bioreductive agents (HABAs), which are also known anticancer agents. The methods described herein may be considered to be methods of enhancing the anticancer activity of AAAs and/or VDAs by co-administering a HABA, or methods of enhancing the anticancer activity of HABAs by co-administering AAAs and/or VDAs.

The administration of the agents described herein may be carried out by any suitable means known to those of skill in the art, with the caveat that the activity of the hypoxia-inducing agent must be as nearly as possible confined to the area that is targeted for treatment, i.e. to a tumor or tumors, or to a region of the body that contains one or more tumors and can be isolated from adjacent areas. VDAs have the capability of preferentially suppressing tumor blood flow without significant compromise of normal circulation (11) and thus may be administered systemically. In this case, the HABA may be administered either locally or systemically, as its activation will be largely confined to the regions of hypoxia within tumors created by the action of the VDA. However, in some embodiments of the invention, administration of VDAs and HABAs is confined largely to a targeted area, i.e. administration is local, such as when combined with embolization. This can be accomplished by locally administering the agents e.g. by intra-arterial injection into the vascular branch supplying a tumor through a catheter placed by interventional radiologists. Such local administration may be carried out by administering individual agents one at a time in close succession as described herein, or by administering a single preparation that contains a mixture of the agents. The administration of AAAs is typically systemic either orally or by intravenous injection after embolization due to the fact that AAAs are used to suppress the compensatory effect, which induce a whole body reaction, of tumor hypoxia induced by VDAs. In other embodiments of the invention, all agents, including the hypoxia-inducing agent (e.g. an AAA and/or VDA) and the HABA, are administered systemically, since activation of the HABA will occur only in the localized hypoxic areas in tumors due to the preferential tumor vascular effect of VDAs. Methods of systemic administration include but are not limited to oral administration, intravenous, intraperitoneal, intramuscular, subcutaneous, or intrearterial administration, inhalation, etc. In yet other embodiments, where embolization is also carried out, the agents (e.g. HABA; or VDA and HABA, with or without an AAA) must be administered first so that they are trapped within the targeted region. However, if hypoxia is induced chemically by VDAs, the hypoxia-inducing agent may be administered either after the HABAs, or together with the HABAs, so long as administration results in sequestering the agents within the targeted region.

The modes of administration are as follows. AAAs are given by systemic administration as the purpose of AAAs is to block the systemic compensatory mechanism. There are two means of administration for HABAs and VDAs in hepatocellular carcinoma. One is by giving VDAs and HABAs intra-arterially with or without embolization, AAAs are then given systemically. This method is used principally for treating hepatocellular carcinoma, which is the only cancer currently using embolization as a standard therapy. The second approach is to give all three agents systemically as VDAs can specifically induce suppression of tumor vessels even given by systemic intravenous injection. This approach will be suitable for patients who are not candidates for embolization. For other solid tumors that are not localized in the liver, embolization is not a standard approach to treat these tumors, and all three agents (HABA, VDAs and AAAs) are typically given systemically by oral, intravenous, intraperitoneal, or subcutaneous route, usually with the sequence of HABAs first, then VDAs and than AAAs afterwards. In this way, HABAs will be distributed to tumors, and then VDAs lead to shutdown of tumor blood flow to induce hypoxia. However, local administration of these agents is also contemplated. The effect of AAAs is much slower and AAAs can be administered afterwards to suppress the compensatory response induced by hypoxia.

Preparations or formulations of the agents described herein are generally suitable for administration to a mammalian patient, and are thus, for example, physiologically compatible. Such compositions include substantially purified forms of the agents, and a pharmacologically or physiologically suitable (compatible) carrier. The preparation of such compositions is generally known to those of skill in the art. Typically, such compositions are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration, e.g.

the agents may be attached to a matrix in order to provide localized delivery. The final amount of each agent in the formulations may vary. However, in general, the amount will be from about 1-99%. As described herein, and depending on the particulars of the treatment protocol, the compositions may contain only one agent, or a mixture of agents (i.e. only HABA or AAA or VDA or an embolizing agent, or any combination of two or more of these). In addition, more than one of each type of agent may be administered in a composition, e.g. one HABA may be administered with two or more VDAs or two of more AAAs, or two or more HABAs may be administered together, etc.

In particular, the invention provides pharmacologically acceptable compositions and/or kits comprising the compositions that include at least one hypoxia-activated bioreductive agent and at least one of a hypoxia-inducing vascular disrupting agent and an anti-angiogenic agent, plus a physiologically acceptable carrier. In other embodiments, compositions comprising at least one hypoxia-activated bioreductive agent and an embolizing agent used during mechanical embolization, e.g. Lipiodol, and, optionally, one or more VDAs and/or AAAs, are also provided.

The types of cancer that may be treated by the methods of the invention include but are not limited to cancers in which solid tumors (solid malignancies) develop, e.g. hepatocellular carcinoma, cholangiocarcinoma, pancreatic cancer, colorectal cancer, anal cancer, lung cancer including small cell or non-small cell lung cancer, breast cancer, prostate cancer, ovarian cancer, testicular cancer, germ cell tumor, renal cell carcinoma, neuroendocrine cancer, gastric cancer, esophageal cancer, head and neck cancer, skin cancer including squamous cell carcinoma or melanoma, soft tissue and osteogenic sarcoma, thyroid cancer, thymoma, bladder cancer, cervical cancer, uterus cancer, central nervous tumor, Hodgkin and non-Hodgkin lymphoma. Both primary and metastatic tumors may be treated by the methods disclosed herein.

The methods of the invention are generally intended to treat mammals, especially humans, but that need not always be the case. Veterinary applications are also contemplated. In addition, those of skill in the art will recognize that other treatment modalities may be combined with the methods of the invention, e.g. surgical removal of tumors or portions of tumors, various chemotherapy regimens, and other treatments of side effects such as treatments for nausea, appetite stimulants, vitamins, etc.

EXAMPLES

Materials and Methods
Cell Lines and Tumor Xenograft Models

Tumor cell lines used in this study include UCI-101 ovarian cancer cells and Hep3B hepatocellular carcinoma cells. Cells are grown in IMEM and DMEM, respectively, supplemented with 10% fetal bovine serum, glutamine, and penicillium/streptomycin in 5% $CO_2$ humidified environment. When cells were grown to 80% confluent, cells were harvested with 1% trypsin and washed with phosphate-buffered saline three times before injected subcutaneously into nude mice. For mouse xenograft studies, $2 \times 10^6$ tumor cells were injected in the back subcutaneously. Nude mice were purchased from NCI Development Therapeutic Program as described. Tumor size was monitored by long and short axes (a and b, respectively) by a caliber and tumor volume was calculated by the formula $ab^2/2$. Treatment with VDA cis-3,4',5-trimethoxy-3'-aminostilbene (stilbene 5c) (50 mg/kg), tirapazamine (60 mg/kg) was done by intraperitoneal injection. Treatment with AAA bevacizumab was done by tail vein injection at a dose of 10 mg/kg.

Determination of Tumor and Normal Organ Perfusion by DCE-MRI

Nude mice with tumor xenografts were anesthetized with 1% isoflurane and mixed oxygen. DEC-MRI was performed with experimental Magnetic Resonance (MR) system (Bruker, Biospec 2.35 T/40 cm) that is dedicated to small animal imaging. Jugular vein was dissected to place an IV catheter for contrast injection in acute phase study. The first batch of mice was injected with 50 µL of gadolinium (OmniScan) through the jugular catheter and MRI images were collected every second to investigate the initial rate of increase of MRI signals immediately after injection. After the initial rate is established, subsequent MRI studies focused on the sustained increase in gadolinium signals, which also provide qualitative and quantitative information for tissue perfusion. For this study, 20 µL of gadolinium was injected directly into tail veins. Mice were transferred into the tunnel of MRI machine within 1 minute after injection. MRI images were collected every minute for 30 min.

Immunohistochemistry Study of Tissue Sections

After mice were sacrificed, major organs and tumors were dissected and fixed in 10% formalin. Tissues were embedded in paraffin and sections were stained with H & E, and with antibody against CD34 for quantification of microvascular density. The scoring of microvascular density was based on the methods described by Weidner et al. by counting the CD34-positive signals in a photo frame of 200× magnification using Nikon ECLIPSE E800M microscope equipped with a Diagnostic Instruments Spot RT CCD camera.

Real-Time Measurement of Changes of Tumor Oxygen and Blood Flow after Treatment with VDAs Nude mice were injected subcutaneously with UCI-101 ovarian cancer cells to form tumor xenografts. Tumor xenografts were subjected to oxygen and blood flow study when tumor size reached 8-10 mm in largest diameter. Tumor was punctured with 25G needle to make a tunnel for insertion of sensor probe. The tip of the sensor probe was left in the center of the tumor. Tumor oxygen level and blood flow were determined by OxyLite 2000 dual channel monitoring system with "bare-fibre" type sensor probe, which is designed for measuring tissue oxygen, temperature and blood flow using laser Doppler technique (Optonix, oxford, UK). The measurement was done in a real time basis (100 measurements per second) and the oxygen level and tumor blood flow were recording continuously. Because the initial trauma induced by needle and insertion of sensor probe can interfere with blood flow and oxygenation, each mouse was recorded first without treatment for at least 20 min before the mice was injected intraperitoneally with the tested VDA cis-3,4',5-trimethoxy-3'-aminostilbene (stilbene 5c) at 50 mg/kg. The tumor blood flow and oxygen level was then recorded for another 20 min after treatment.

Example 1

Suppression of Tumor Vasculature by Stilbene 5c

Figure 1B:
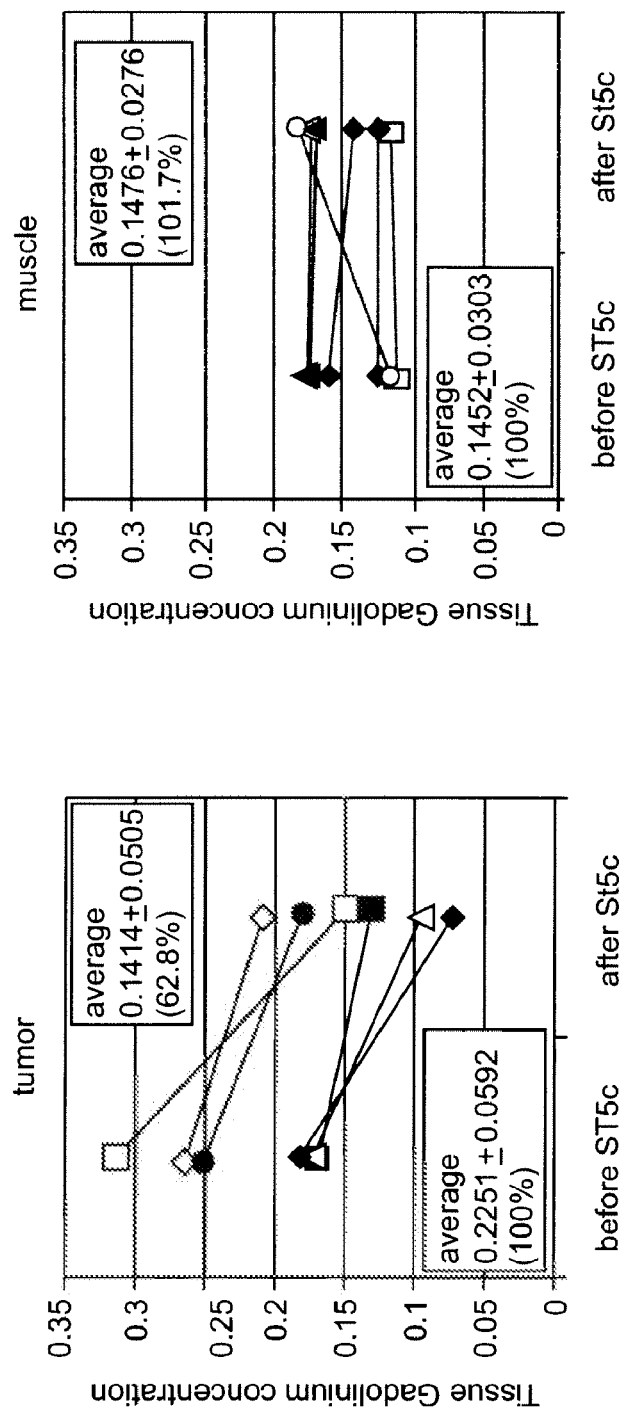

Stilbene 5c was investigated to examine whether it can suppress tumor blood flow and eventually lead to tumor hypoxia. A rapid kinetic study showed that after 10 min of rapid increase the gadolinium signals reached plateau and persisted for at least 30 min without washing out (11). We chose 30 min after injection for studying the images in plateau, and compare same tumor of the same mice before and after stilbene treatment to avoid any variation among mice. Mice were first imaged without contrast to obtain a baseline (FIG. 1, left upper panel). The section was obtained at the center of the tumor. Kidney in the same section was used as an internal organ control from tumor in the same mice. After injected with 20 µl of gadolinium (OmniScan) via the tail vein, mice were analyzed with a rapid sequence MRI every minute for total of 30 min. Both tumor and kidney exhibited enhancement of MRI signals after injection of gadolinium, which represented vascular perfusion of tumor and kidney (FIG. 1 right upper panel). Mice were then left for at least 24 hours to let gadolinium washed out. Same mice were treated with 50 mg/kg stilbene 5c by intraperitoneal injection on the second or third day. Four hours after injection of stilbene 5c, mice were imaged again before and after gadolinium injection by the same protocol and compared with the previous pair of images before stilbene treatment. In the baseline image before gadolinium injection, the T1-weighted image had a slight increase of MRI signals (FIG. 1, left lower panel) compared with the baseline image of untreated mice. This increased signal was likely due to a small amount of residual gadolinium left in the body from the previous day. After injection of gadolinium, kidney and other normal organs showed enhanced signals. However, the tumor region showed significantly less gadolinium enhancement compared with that before stilbene treatment (FIG. 1, right panels), suggesting that stilbene 5c selectively inhibits tumor perfusion and spares normal organs. Similar studies were performed in 6 mice and the T1 map was generated for each mouse. The concentration of gadolinium was calculated from each image and results are shown in FIG. 1. The algorithm of calculation failed in kidney due to the fact that the signals in kidney reached saturation. The concentration of gadolinium in tumor decreased to an average of 62.8% in tumor at 4 hours after stilbene treatment. In contrast, the concentration of gadolinium in muscle did not change with stilbene treatment, indicating that stilbene 5c selectively suppresses tumor perfusion without compromising normal vascular perfusion.

Example 2

Figure 2A:
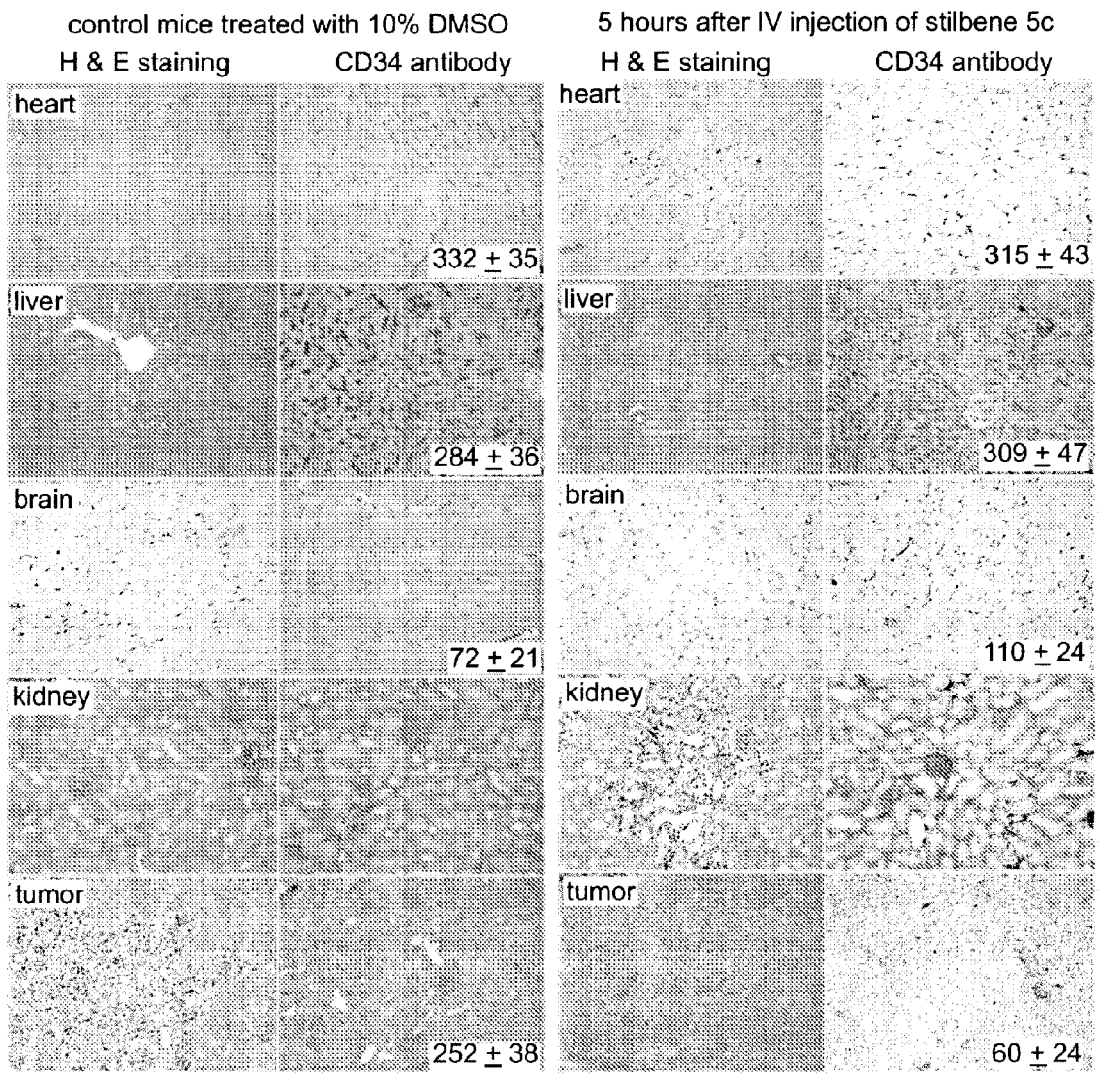
FIGS. 2A-B. Stilbene 5c treatment decreases microvascular density in tumor but not in normal organs. Nude mice with UCI tumor xenograft were treated with 10% DMSO or stilbene 5c at 50 mg/kg intraperitoneally. Mice were sacrificed at 4 hours after injection, and various organs and tumor were harvested for fixation and standard hematoxylin and eosin (H & E) staining. Immunohistochemical staining of each section was performed with anti-CD34 antibody to quantify the microvascular density. In the original immunohistochemical stained sections, brown staining indicated a positive signal for CD34 staining. (A) Shown are the black and white pictures in 200× fold magnification. The numbers of positive signals in each CD34 stained picture are counted and are shown in the right lower corner of each panel. (B) The averages and standard deviations of 4 different fields that show the most abundant microvascular density are plotted in a histogram. The sections from kidney cannot be scored due to the fact that all vessels around renal tubules are fused into a large network in the picture. These results suggest that tumor vascular density was dramatically decreased by nearly 4 fold, whereas that of other organs, heart, liver, brain and kidney was not affected by stilbene 5c treatment.
Figure 2B:
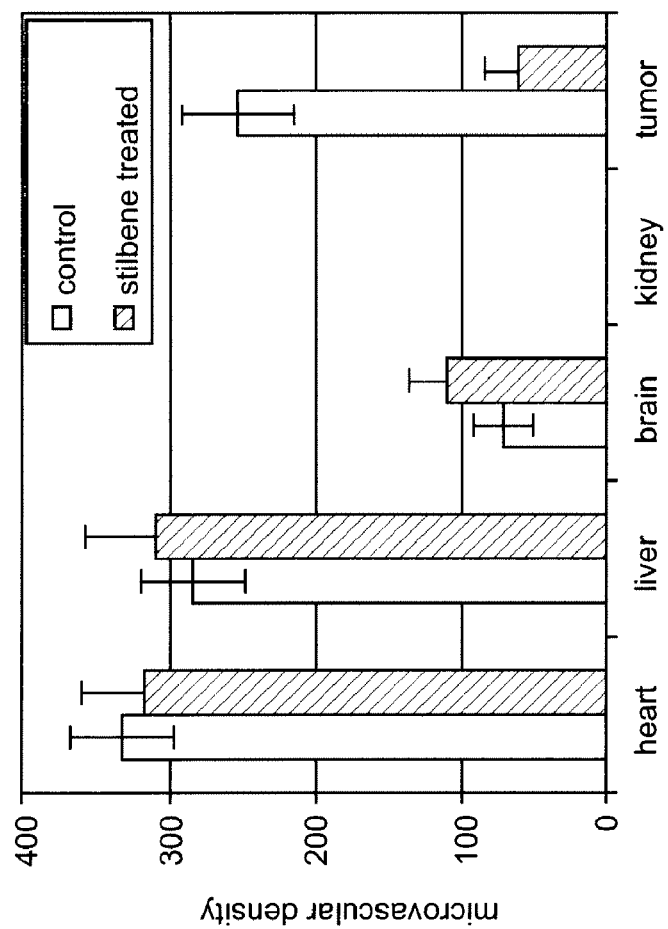

Immunohistochemistry Staining with CD34 Vascular Marker in Sections of Tumor and Normal Organs We took tissues that were studied with DCE-MRI to investigate the vascular density of tumor and correlate with the results from DCE-MRI-derived vascular perfusion studies. We particularly examined sections from heart and brain, where the toxicity of colchicine site inhibitors was observed. Tissue sections were stained with standard H & E and anti-CD34 (an endothelial marker) antibody by immunohistochemistry staining. The H & E staining did not show any significant changes in any major organs after stilbene 5c treatment (FIG. 2). There was also no histological difference in tumor either. We then used anti-CD34 staining to score microvascular density in tumor and various normal organs (54, 55). The results are indicated at the right lower corner of each panel except kidney, which cannot be scored due to fusion of the capillary network rather than discrete dots or tubes in appearance. Treatment with stilbene 5c does not change the microvascular density of heart, liver, kidney and brain, but significantly decrease that of tumor to nearly one fourth (FIG. 2). This finding is consistent with our MRI result that stilbene 5c selectively decreased tumor vascular perfusion without compromising normal organ perfusion.

Example 3

Induction of Tumor Hypoxia by Representative VDA Stilbene 5c to Facilitate Activation of Tirapazamine In this study, we performed proof of concept study with VDA stilbene 5c to confirm that stilbene 5c induce tumor hypoxia. Previously in Example 1, we have used dynamic contrast-enhanced MRI study to prove that stilbene 5c can successfully inhibit tumor blood flow. However, the technique of DCE-MRI study cannot be used as a continuous monitoring tool and could not record how fast stilbene 5c induces suppression of tumor blood flow and how fast it can induce tumor hypoxia. To achieve the purpose of real time monitoring, we use oxygen and blood flow sensor to record the real time changes within the first 20 min after mice are treated with stilbene 5c.

Figure 3:
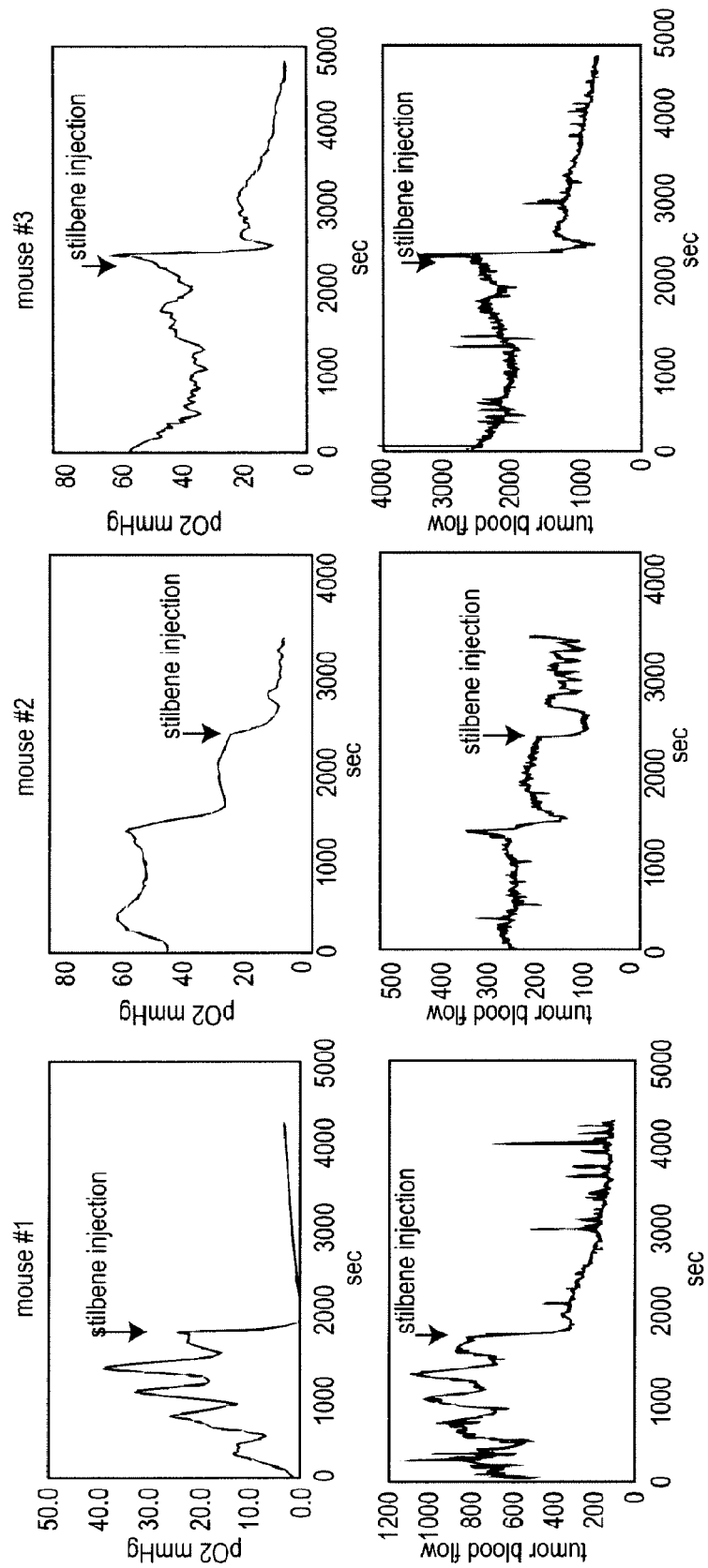
FIG. 3. Tumor blood flow and oxygen content in tumor. Oxygen and blood flow were monitored by OxyFlo and OxyLite system (Optronix, Oxford, UK). Mice were anesthetized with isoflurane and a triple sensor that records temperature, oxygen and blood flow was inserted into tumor and left for 1 hour for recording. Shown are the results of three mice with similar size subcutaneous tumors derived from UCI-101 ovarian cancer cells. Top panels are oxygen level and lower panels are tumor blood flow. Timing of St5c injection was marked.

There are several issues that need to be considered in order to interpret the results. Tumor blood flow and tumor oxygen level are dependent on the location of the probe in the tumor. The more peripheral the location of the probe is, the higher the blood flow and oxygen level will be. The center portion will have lower blood flow and hence more hypoxia in general. It is very difficult to compare different mice due to individual variation and the location of tumor in which the sensor probe is placed for the study. The most reliable way to interpret the result is to use the pre-treatment blood flow and oxygen level as its own control to compare with the post-treatment result since the sensor probe was kept in the same position to eliminate spatial variation. All mice were thus recorded for at least 20 min to record the pre-treatment baseline. In the baseline study, it was observed that there is a significant temporal variation as shown in FIG. 3. The baseline oxygenation and tumor blood flow show a synchronized fluctuated baseline with time. When the tumor blood flow increases, the oxygen level increases correspondingly. After we did a continuous monitoring for at least 20 min to establish this temporal variation, stilbene 5c was injected followed by continuous monitoring for another 20-30 min to examine the effect of stilbene in tumor oxygenation and blood flow in real time. It was noted that different tumors had very different tumor blood flow and oxygenation level as shown in the three mice here (FIG. 3). Mouse #1 had a big fluctuation in baseline in a cyclic pattern with blood flow between 600-1100 and oxygen level between 15-40 mm Hg. Note that the first 10 min results were not taken into consideration due to adjustment of the trauma from probe insertion. Mouse #2 has a tumor blood flow between 200-300 and oxygen levels have two plateaus. One plateau is at 50-60 mm Hg and then dropped to 20-30 mm Hg at the subsequent plateau. Mouse #3 has a very high tumor blood flow between 2000-3000 and oxygen levels at 35-55 mm Hg range. After stilbene 5c (50 mg/kg) treatment by intraperitoneal injection, all three mice exhibited a dramatic decrease in tumor oxygen level down to less than 10 mm Hg before the recording stopped. Tumor blood flow decreased to less than 25% of the level before stilbene treatment in mice #1 and 3. The tumor blood flow change in mouse #2 was significant in the beginning but subsequently recovered in some degree though still lower than baseline blood flow level. These results suggest the following findings. (a) Stilbene treatment is effective in inducing hypoxia in tumor. (b) The lower the initial tumor blood flow, the less effective in stilbene induced suppression of tumor blood flow. This could be explained by an explanation that less tumor blood flow leads to less drug delivery to tumor bed and less effective in decreasing tumor perfusion. (c) There are significant temporal and spatial variations in tumor blood flow. Our study is limited to one single spot in tumor to eliminate the spatial variation.

Example 4

Enhancing the Effect of Stilbene 5c by Bevacizumab

Figure 4:
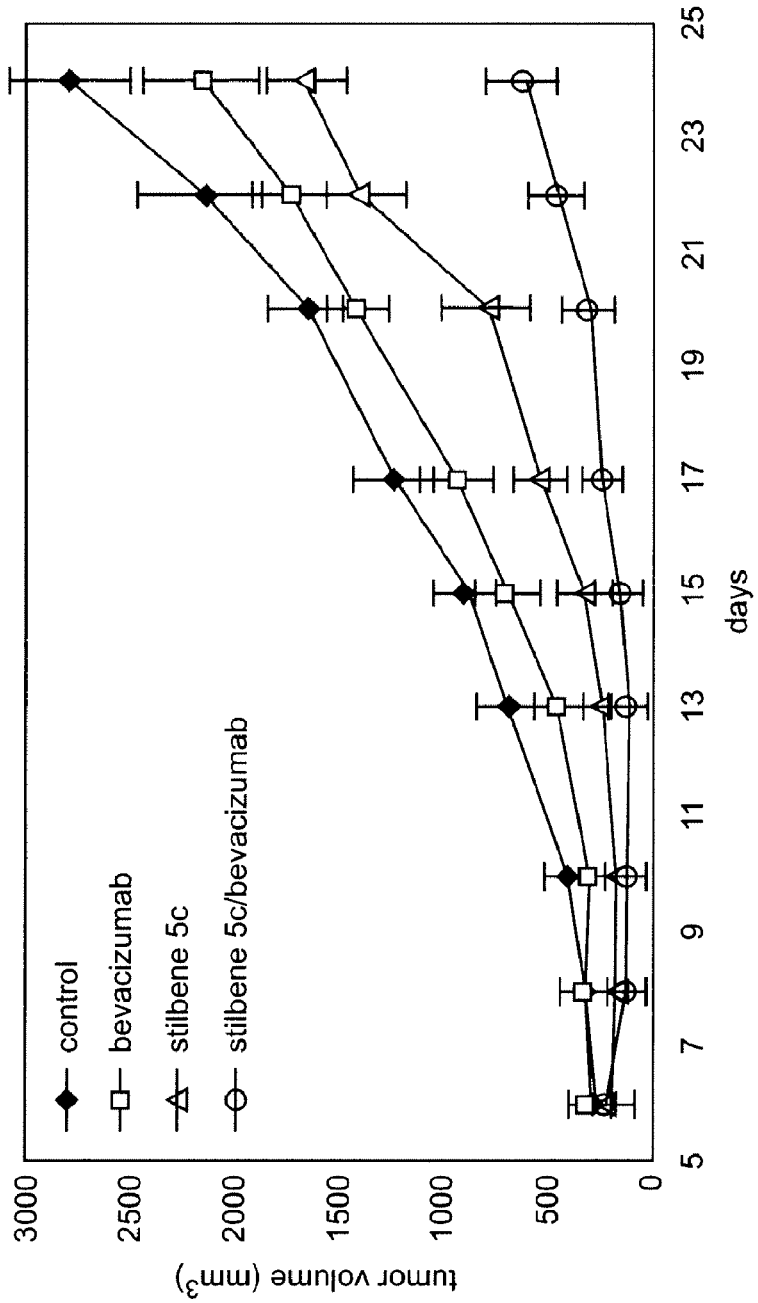
FIG. 4. Efficacy of stilbene 5c in vivo and enhanced effect by bevacizumab. Nude mice were injected with UCI-101 cells subcutaneously and mice are treated with stilbene 5c at 20 mg/kg/day Monday-Friday with or without bevacizumab 10 mg/kg twice a week. Tumor volume was calculated by the long and short axes. Each group contains 8 mice and the average tumor volumes and standard deviations were plotted against days.

Next we used ovarian cancer UCI101 cells to study the in vivo efficacy of stilbene 5c We first administered stilbene 5c with intraperitoneal injection at 25 mg/kg three times a week. Tumor volume was calculated by measuring the long and short axes. Unfortunately, we did not detect any difference in tumor growth between control and stilbene 5c-treated mice. The result suggests that administration of stilbene 5c at three times a week may not be the right way of dosing. The failure could be due to the possibility that intermittent dosing leaves a viable rim of tumor, which survives the treatment of VDAs by getting nutritional and blood support from surrounding normal vasculature. When treatment with VDAs is stopped, the viable rim of tumor grows quickly. Tumor vasculature recovers quickly by recruitment of the mobilized endothelial progenitor cells. Based on this rationale, we combined stilbene 5c with bevacizumab, which was used to neutralize VEGF secreted by UCI-101 tumor cells. To achieve a better therapeutic efficacy, we also increased the frequency of stilbene 5c treatment to five consecutive days (Monday to Friday) for two weeks at 20 mg/kg/day. Bevacizumab was given at 10 mg/kg twice a week (Mondays and Fridays) for 5 doses. The group treated with stilbene 5c alone had tumor growth suppression about 45%, and the group treated with bevacizumab alone had tumor growth suppression at about 25%. The group treated with combination of stilbene 5c and bevacizumab achieved 80% tumor growth suppression (FIG. 4). After dissection of the tumor at 24 clays, tumors were weighed and the results confirmed the measurement result (not shown). This study leads to two conclusions. Stilbene 5c is more effective if given more frequently and stilbene 5c is much more effective when combined with angiogenic inhibitor bevacizumab.

Example 5

Combining Tirapazamine with Stilbene 5c

Figure 5A:
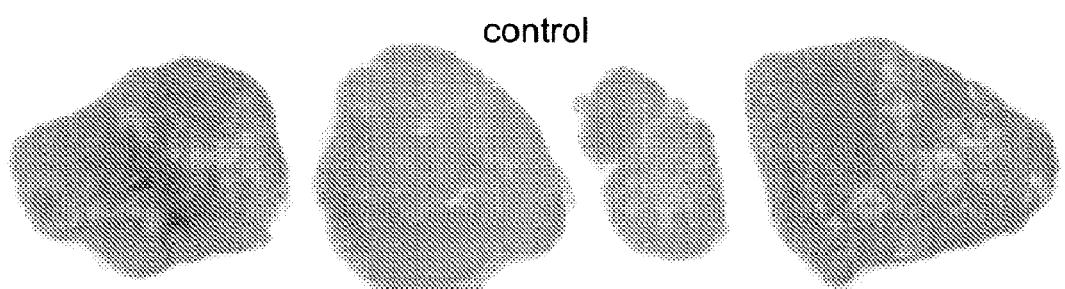
FIGS. 5A-D. Synergism between tirapazamine and stilbene 5c. Nude mice with UCI101 tumor xenograft were treated with vehicle (5A, control), tirapazamine alone (5B), stilbene 5c (50 mg/kg) alone (5C) or tirapazamine (60 mg/kg) followed by stilbene 5c (50 mg/kg) (5D) to induce tumor hypoxia. Mice were sacrificed three days later and tumors were harvested for H&E section. Shown are the low power views of tumor sections. The portion of tumor that stained darker is viable, whereas the portion in lighter color is the necrotic area. Please note that in the tumor section at the right lower panel in the combination group. The majority of the tumor is necrotic, and only a small portion of tumor in the center and peripheral rim remain viable. The central viable portion is proximal to the branches of larger vessels.
Figure 5B:
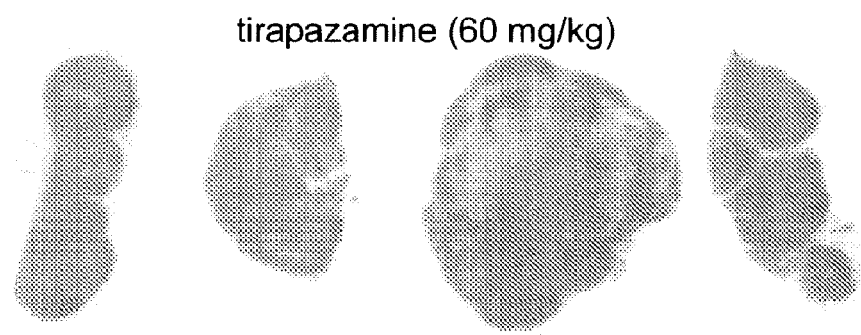
Figure 5C:
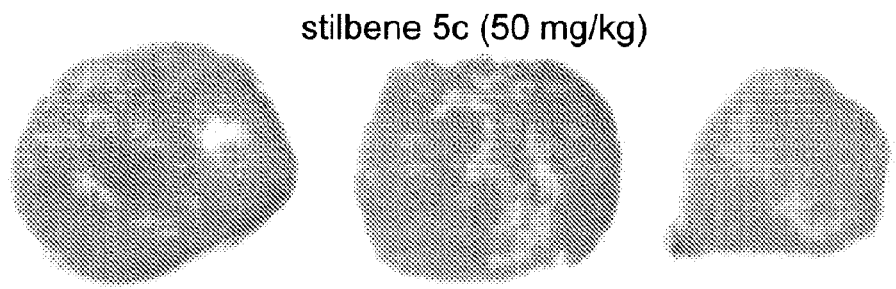
Figure 5D:
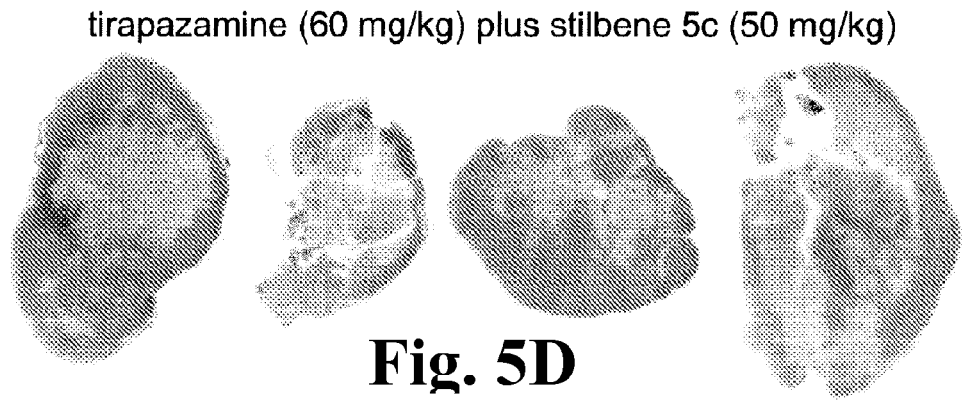

Next tirapazamine was combined with stilbene 5c for a proof-of-principle study. Nude mice with established UCI101 tumor xenografts (tumor size about 1 cm in the long axis) were treated with tirapazamine at 60 mg/kg intraperitoneally first. After 60 min, stilbene 5c was administered intraperitoneally at 50 mg/kg, which has been established to be capable of inducing profound tumor hypoxia within minutes (FIG. 3). As discussed earlier, the sequence of giving tirapazamine first to allow its distribution to tumor before administration of stilbene 5c to shut down tumor perfusion is absolutely critical. Mice were then sacrificed three days later. Tumors were harvested and the center portion of tumor was sliced and analyzed with histological section and H&E staining. Previously it was known that tirapazamine alone given at 70 mg/kg has no effect in tumor growth suppression, hence tirapazamine alone group (FIG. 5B) was not expected to have any effect. As shown in FIG. 5, the control tumor (FIG. 5A) and tumor treated with stilbene 5c (FIG. 5C) have very small areas of tumor necrosis. In the combination group in which tirapazamine was given 60 min before stilbene 5c, which allows distribution of tirapazamine into the tumor first, followed by induction of tumor hypoxia by stilbene 5c, we observed a dramatic increase in the size of the area of necrosis in the tumor (FIG. 5D). Most importantly, the necrosis area is mainly in the center of tumor with sparing of a peripheral rim, suggesting that the necrosis is due to the effect of hypoxia, since the peripheral portion of the tumor can obtain blood and oxygen supply by diffusion from the surrounding normal tissue. This finding supports our theory that combination of tirapazamine followed by stilbene 5c to induce tumor hypoxia can have a synergistic effect and enhance the therapeutic efficacy of either agent.

Next we measured the size of tumor xenografts after multiple dosing. Nude mice were injected subcutaneously with UCI-101 cells and tumor became visible after day 7. Treatment was administered by intraperitoneal injection on days 8, 10 and 12 with 6 mice in each group. The dose of stilbene 5c was 50 mg/kg and that of tirapazamine was 60 mg/kg. However, at day 14, the two group of mice treated with tirapazamine developed a weight loss of 20% and all mice were thus sacrificed for comparison. The results of tumor volume are presented in FIG. 6. The size of tumor of the groups treated with stilbene 5c or tirapazamine showed a decrease to about 50% in average compared with the control, whereas the group treated with stilbene 5c and tirapazamine was further suppressed to 27% of the control. This result suggests that stilbene 5c and tirapazamine are at least additive and could be even synergistic.

Example 6

Combination of Tirapazamine and Anti-Angiogenic Agent Bavacizumab

Figure 6:
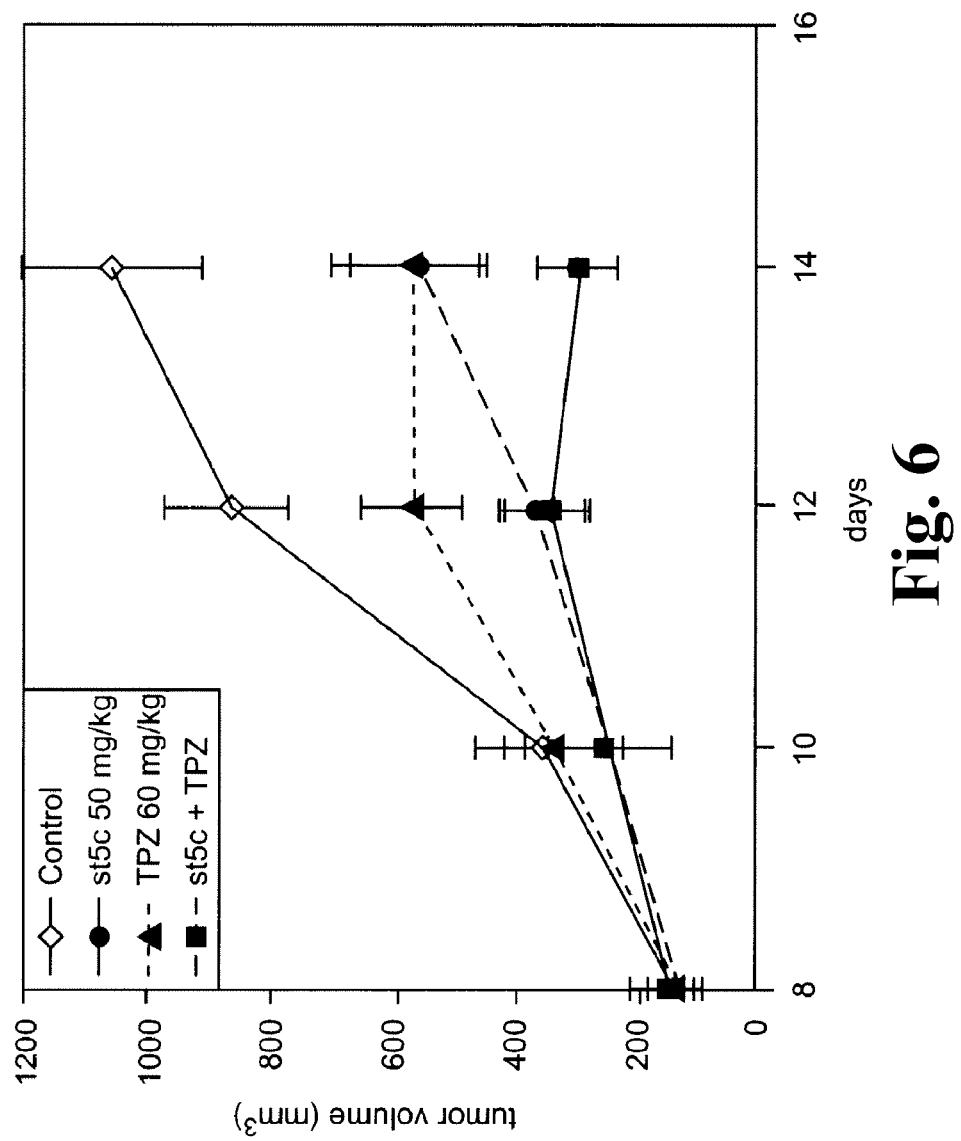
FIG. 6. Synergistic effect of stilbene 5c and tirapazamine. Nude mice with subcutaneous tumors were treated with (1) normal saline control, (2) stilbene 5c at 50 mg/kg, (3) tirapazamine 60 mg/kg, (4) combination of stilbene 5c and tirapazamine at days 8, 10, and 12 by intraperitoneal injection. Mice were then sacrificed at day 14 due to weight loss. The long and short axes of tumor were measured to calculate tumor size and plotted against days. Each treatment group contains 6 mice.
Figure 7:
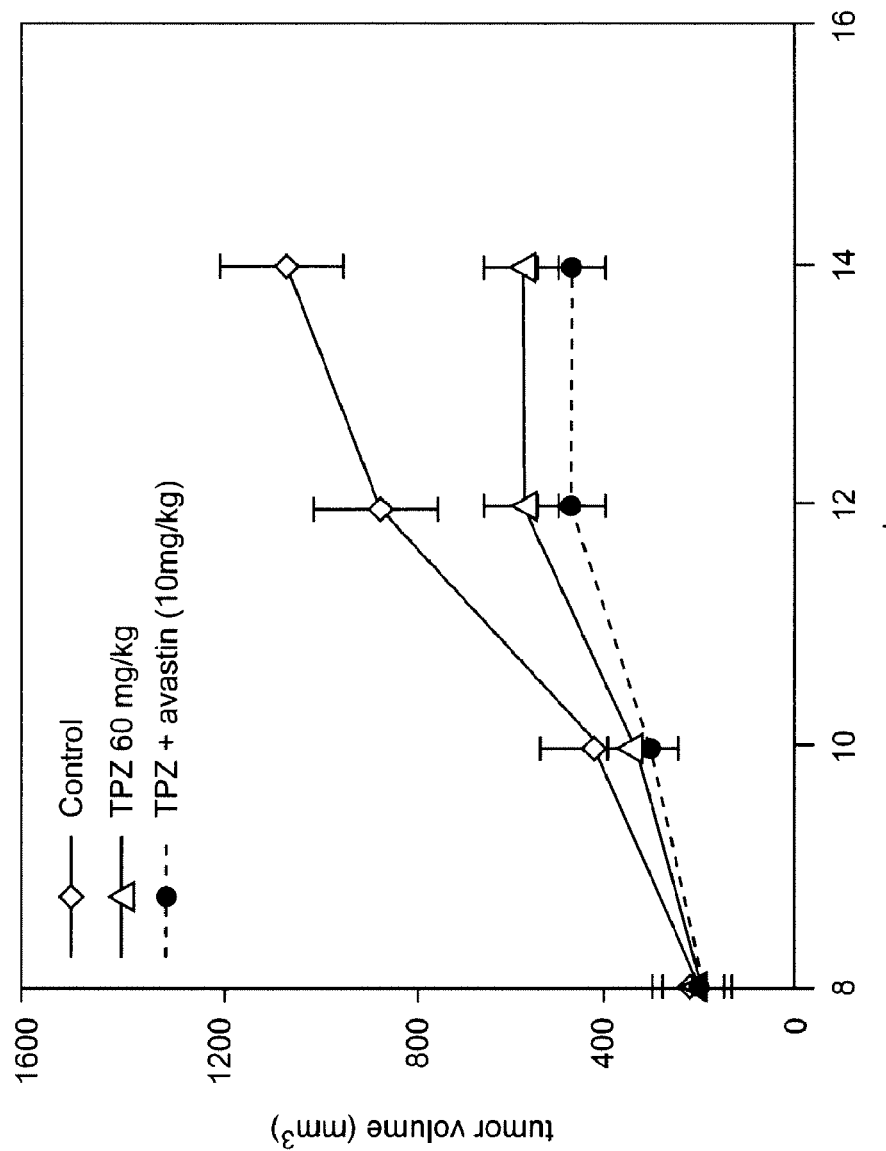
FIG. 7. Combination of tirapazamine and bevacizumab. Nude mice with subcutaneous tumors were treated with (1) normal saline control, (2) tirapazamine 60 mg/kg at days 8, 10 and 12, (3) combination of tirapazamine at days 8, 10 and 12 and bevacizumab (10 mg/kg) at days 8 and 11. Mice were then sacrificed at day 14. The long and short axes of tumors were measured to calculate tumor size and plotted against days. Each treatment group contains 6 mice.

Based on the rationale that anti-angiogenic agent could suppress tumor vasculature and make tumor hypoxia, we examine if there is any synergism between tirapazamine and anti-angiogenic agent bevacizumab. Nude mice with the same UCI-101 tumor xenografts were treated with tirapazamine and bevacizumab similar to the study with tirapazamine and stilbene 5c. Mice with established tumor were treated with tirapazamine at days 8, 10, and 12 intraperitoneally, and bevacizumab at 10 mg/kg at days 8 and 11 by intravenous injection through tail veins. Tumor xenografts were measured and sizes are plotted in FIG. 7. There were minimal improvement of tumor size shrinkage when bevacizumab was added, which is in contrast with the difference between tirapazamine alone versus the combination of tirapazamine and stilbene 5c (FIG. 6). There was no statistically significant difference between the tirapazamine group versus the tirapazamine and bevacizumab group. There are several potentially explanations for this phenomenon. One is that the effect of anti-angiogenic activity is much slower than vascular disrupting agent stilbene 5c, which induce almost immediate vascular shut down. In contrast, bevacizumab neutralizes VEGF and could take a longer duration of treatment to result in tumor hypoxia. Second, according to the theory of vascular normalization by Jain et al., the anti-angiogenic agent bevacizumab first induces vascular normalization in tumor (51-53). Therefore, the tumor oxygen level may even improve, instead of being suppressed, due to vascular normalization and could not enhance the therapeutic benefit of tirapazamine. Utilization of anti-angiogenic agent bevacizumab with tirapazamine will need to combine with stilbene VDA, which was confirmed to be more effective in induce tumor growth suppression. One possible way to use the three drug combination is to use tirapazamine and stilbene vascular disrupting agent in the initial setting followed by a maintenance therapy with bevacizumab.

REFERENCES

1. Eberhard, A., Kahlert, S., Goede, V., Hemmerlein, B., Plate, K. H., and Augustin, H. G. Heterogeneity of angiogenesis and blood vessel maturation in human tumors: implications for antiangiogenic tumor therapies. Cancer Res, 60: 1388-1393, 2000.
2. McDonald, D. M. and Choyke, P. L. Imaging of angiogenesis: from microscope to clinic. Nat Med, 9: 713-725, 2003.
3. Carmeliet, P. and Jain, R. K. Angiogenesis in cancer and other diseases. Nature, 407: 249-257, 2000.
4. Bikfalvi, A. and Bicknell, R. Recent advances in angiogenesis, anti-angiogenesis and vascular targeting. Trends Pharmacol Sci, 23: 576-582, 2002.
5. Augustin, H. G. Translating angiogenesis research into the clinic: the challenges ahead. Br J Radiol, 76 Spec No 1: S3-10, 2003.
6. Collins, T. S, and Hurwitz, H. I. Targeting vascular endothelial growth factor and angiogenesis for the treatment of colorectal cancer. Semin Oncol, 32: 61-68, 2005.
7. Gerber, H. P. Anti-angiogenesis: biology is the foundation for therapy. Drug Discov Today, 8: 344-346, 2003.
8. Sato, Y. Molecular diagnosis of tumor angiogenesis and anti-angiogenic cancer therapy. Int J Clin Oncol, 8: 200-206, 2003.
9. Tozer, G. M., Kanthou, C., and Baguley, B. C. Disrupting tumour blood vessels. Nat Rev Cancer, 5: 423-435, 2005.
10. Neri, D. and Bicknell, R. Tumour vascular targeting. Nat Rev Cancer, 5: 436-446, 2005.
11. Durrant, D., Corwin, F., Simoni, D., Zhao, M., Rudek, M. A., Salloum, F. N., Kukreja, R. C., Fatouros, P. P., and Lee, R. M. cis-3,4',5-Trimethoxy-3'-aminostilbene disrupts tumor vascular perfusion without damaging normal organ perfusion. Cancer Chemother Pharmacol, 63: 191-200, 2009.
12. Durrant, D., Richards, J. E., Walker, W. T., Baker, K. A., Simoni, D., and Lee, R. M. Mechanism of cell death induced by cis-3,4',5-trimethoxy-3'-aminostilbene in ovarian cancer. Gynecol Oncol, 110: 110-117, 2008.
13. Durrant, D. E., Richards, J., Tripathi, A., Kellogg, G. E., Marchetti, P., Eleopra, M., Grisolia, G., Simoni, D., and Lee, R. M. Development of water soluble derivatives of cis-3,4',5-trimethoxy-3'-aminostilbene for optimization and use in cancer therapy. Invest New Drugs, 27: 41-52, 2009.
14. Maxwell, P. H., Pugh, C. W., and Ratcliffe, P. J. Activation of the HIF pathway in cancer. Curr Opin Genet Dev, 11: 293-299, 2001.
15. Fong, G. H. Mechanisms of adaptive angiogenesis to tissue hypoxia. Angiogenesis, 11: 121-140, 2008.
16. Manukhina, E. B., Downey, H. F., and Mallet, R. T. Role of nitric oxide in cardiovascular adaptation to intermittent hypoxia. Exp Biol Med (Maywood), 231: 343-365, 2006.
17. Cawley, S. M., Sawyer, C. L., Brunelle, K. F., van der Vliet, A., and Dostmann, W. R. Nitric oxide-evoked transient kinetics of cyclic GMP in vascular smooth muscle cells. Cell Signal, 19: 1023-1033, 2007.
18. Fukumura, D. and Jain, R. K. Role of nitric oxide in angiogenesis and microcirculation in tumors. Cancer Metastasis Rev, 17: 77-89, 1998.
19. Ziche, M. and Morbidelli, L. Nitric oxide and angiogenesis. J Neurooncol, 50: 139-148, 2000.
20. Shaked, Y., Ciarrocchi, A., Franco, M., Lee, C. R., Man, S., Cheung, A. M., Hicklin, D. J., Chaplin, D., Foster, F. S., Benezra, R., and Kerbel, R. S. Therapy-induced acute recruitment of circulating endothelial progenitor cells to tumors. Science, 313: 1785-1787, 2006.
21. Brown, J. M. SR 4233 (tirapazamine): a new anticancer drug exploiting hypoxia in solid tumours. Br J Cancer, 67: 1163-1170, 1993.
22. Denny, W. A. and Wilson, W. R. Tirapazamine: a bioreductive anticancer drug that exploits tumour hypoxia. Expert Opin Investig Drugs, 9: 2889-2901, 2000.
23. Gatzemeier, U., Rodriguez, G., Treat, J., Miller, V., von Roemeling, R., Viallet, J., and Rey, A. Tirapazamine-cisplatin: the synergy. Br J Cancer, 77 Suppl 4: 15-17, 1998.
24. Cahill, A., Jenkins, T. C., Pickering, P., and White, I. N. Genotoxic effects of 3-amino-1,2,4-benzotriazine-1,4-dioxide (SR 4233) and nitrogen mustard-N-oxide (nitromin) in Walker carcinoma cells under aerobic and hypoxic conditions. Chem Biol Interact, 95: 97-107, 1995.
25. Cahill, A., Jenkins, T. C., and White, I. N. Metabolism of 3-amino-1,2,4-benzotriazine-1,4-dioxide (SR 4233) by purified DT-diaphorase under aerobic and anaerobic conditions. Biochem Pharmacol, 45: 321-329, 1993.
26. Cahill, A. and White, I. N. Reductive metabolism of 3-amino-1,2,4-benzotriazine-1,4-dioxide (SR 4233) and the induction of unscheduled DNA synthesis in rat and human derived cell lines. Carcinogenesis, 11: 1407-1411, 1990.
27. Cahill, A. and White, I. N. Reductive activation of N-oxides to cause DNA strand breakage in cell lines in vitro. Biochem Soc Trans, 19: 127S, 1991.
28. White, I. N., Cahill, A., Davies, A., and Carthew, P. Acute lesions in rats caused by 3-amino-1,2,4-benzotriazine-1,4-dioxide (SR 4233) or nitromin: a comparison with rates of reduction in microsomal systems from target organs. Arch Toxicol, 66: 100-106, 1992.
29. Costa, A. K., Baker, M. A., Brown, J. M., and Trudell, J. R. In vitro hepatotoxicity of SR 4233 (3-amino-1,2,4-benzotriazine-1,4-dioxide), a hypoxic cytotoxin and potential antitumor agent. Cancer Res, 49: 925-929, 1989.
30. Senan, S., Rampling, R., Graham, M. A., Wilson, P., Robin, H., Jr., Eckardt, N., Lawson, N., McDonald, A., von Roemeling, R., Workman, P., and Kaye, S. B. Phase I and pharmacokinetic study of tirapazamine (SR 4233) administered every three weeks. Clin Cancer Res, 3: 31-38, 1997.
31. Graham, M. A., Senan, S., Robin, H., Jr., Eckhardt, N., Lendrem, D., Hincks, J., Greenslade, D., Rampling, R., Kaye, S. B., von Roemeling, R., and Workman, P. Pharmacokinetics of the hypoxic cell cytotoxic agent tirapazamine and its major bioreductive metabolites in mice and humans: retrospective analysis of a pharmacokinetically guided dose-escalation strategy in a phase I trial. Cancer Chemother Pharmacol, 40: 1-10, 1997.
32. Miller, V. A., Ng, K. K., Grant, S. C., Kindler, H., Pizzo, B., Heelan, R. T., von Roemeling, R., and Kris, M. G. Phase II study of the combination of the novel bioreductive agent, tirapazamine, with cisplatin in patients with advanced non-small-cell lung cancer. Ann Oncol, 8: 1269-1271, 1997.

33. Bedikian, A. Y., Legha, S. S., Eton, O., Buzaid, A. C., Papadopoulos, N., Coates, S., Simmons, T., Neefe, J., and von Roemeling, R. Phase II trial of tirapazamine combined with cisplatin in chemotherapy of advanced malignant melanoma. Ann Oncol, 8: 363-367, 1997.

34. Maluf, F. C., Leiser, A. L., Aghajanian, C., Sabbatini, P., Pezzulli, S., Chi, D. S., Wolf, J. K., Levenback, C., Loh, E., and Spriggs, D. R. Phase II study of tirapazamine plus cisplatin in patients with advanced or recurrent cervical cancer. Int J Gynecol Cancer, 16: 1165-1171, 2006.

35. Covens, A., Blessing, J., Bender, D., Mannel, R., and Morgan, M. A phase II evaluation of tirapazamine plus cisplatin in the treatment of recurrent platinum-sensitive ovarian or primary peritoneal cancer: a Gynecologic Oncology Group study. Gynecol Oncol, 100: 586-590, 2006.

36. Williamson, S. K., Crowley, J. J., Lara, P. N., Jr., McCoy, J., Lau, D. H., Tucker, R. W., Mills, G. M., and Gandara, D. R. Phase III trial of paclitaxel plus carboplatin with or without tirapazamine in advanced non-small-cell lung cancer: Southwest Oncology Group Trial S0003. J Clin Oncol, 23: 9097-9104, 2005.

37. McKeown, S. R., Cowen, R. L., and Williams, K. J. Bioreductive drugs: from concept to clinic. Clin Oncol (R Coll Radiol), 19: 427-442, 2007.

38. Seow, H. A., Penketh, P. G., Shyam, K., Rockwell, S., and Sartorelli, A. C. 1,2-Bis(methylsulfonyl)-1-(2-chloroethyl)-2-[[1-(4-nitrophenyl)ethoxy]carbonyl]hydrazine: an anticancer agent targeting hypoxic cells. Proc Natl Acad Sci USA, 102: 9282-9287, 2005.

39. Papadopoulou, M. V., Ji, X., and Bloomer, W. D. Potentiation of alkylating agents by NLCQ-1 or TPZ in vitro and in vivo. J Exp Ther Oncol, 5: 261-272, 2006.

40. Del Pozo, A. C. and Lopez, P. Management of hepatocellular carcinoma. Clin Liver Dis, 11: 305-321, 2007.

41. Blum, H. E. and Spangenberg, H. C. Hepatocellular carcinoma: an update. Arch Iran Med, 10: 361-371, 2007.

42. Reidy, D. L. and Schwartz, J. D. Therapy for unresectable hepatocellular carcinoma: review of the randomized clinical trials-I: hepatic arterial embolization and embolization-based therapies in unresectable hepatocellular carcinoma. Anticancer Drugs, 15: 427-437, 2004.

43. Bruix, J., Sala, M., and Llovet, J. M. Chemoembolization for hepatocellular carcinoma. Gastroenterology, 127: S 179-188, 2004.

44. Davis, P. D., Dougherty, G. J., Blakey, D. C., Galbraith, S. M., Tozer, G. M., Holder, A. L., Naylor, M. A., Nolan, J., Stratford, M. R., Chaplin, D. J., and Hill, S. A. ZD6126: a novel vascular-targeting agent that causes selective destruction of tumor vasculature. Cancer Res, 62: 7247-7253, 2002.

45. Segreti, J. A., Polakowski, J. S., Koch, K. A., Marsh, K. C., Bauch, J. L., Rosenberg, S. H., Sham, H. L., Cox, B. F., and Reinhart, G. A. Tumor selective antivascular effects of the novel antimitotic compound ABT-751: an in vivo rat regional hemodynamic study. Cancer Chemother Pharmacol, 54: 273-281, 2004.

46. Masunaga, S., Nagasawa, H., Nagata, K., Suzuki, M., Uto, Y., Hori, H., Kinashi, Y., and Ono, K. Dependency of the effect of a vascular disrupting agent on sensitivity to tirapazamine and gamma-ray irradiation upon the timing of its administration and tumor size, with reference to the effect on intratumor quiescent cells. J Cancer Res Clin Oncol, 133: 47-55, 2007.

47. Ma, W. W. and Adjei, A. A. Novel agents on the horizon for cancer therapy. CA Cancer J Clin, 59: 111-137, 2009.

48. Folkman, J. Angiogenesis. Annu Rev Med, 57: 1-18, 2006.

49. Folkman, J. Antiangiogenesis in cancer therapy—endostatin and its mechanisms of action. Exp Cell Res, 312: 594-607, 2006.

50. Ruegg, C. and Mutter, N. Anti-angiogenic therapies in cancer: achievements and open questions. Bull Cancer, 94: 753-762, 2007.

51. Willett, C. G., Kozin, S. V., Duda, D. G., di Tomaso, E., Kozak, K. R., Boucher, Y., and Jain, R. K. Combined vascular endothelial growth factor-targeted therapy and radiotherapy for rectal cancer: theory and clinical practice. Semin Oncol, 33: S35-40, 2006.

52. Jain, R. K. Antiangiogenic therapy for cancer: current and emerging concepts. Oncology (Williston Park), 19: 7-16, 2005.

53. Jain, R. K., Tong, R. T., and Munn, L. L. Effect of vascular normalization by antiangiogenic therapy on interstitial hypertension, peritumor edema, and lymphatic metastasis: insights from a mathematical model. Cancer Res, 67: 2729-2735, 2007.

54. Weidner, N., Folkman, J., Pozza, F., Bevilacqua, P., Allred, E. N., Moore, D. H., Meli, S., and Gasparini, G. Tumor angiogenesis: a new significant and independent prognostic indicator in early-stage breast carcinoma. J Natl Cancer Inst, 84: 1875-1887, 1992.

55. Weidner, N., Semple, J. P., Welch, W. R., and Folkman, J. Tumor angiogenesis and metastasis—correlation in invasive breast carcinoma. N Engl J Med, 324: 1-8, 1991.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of treating a solid tumor in a subject, comprising administering to the subject a hypoxia-activated bioreductive agent and one or more hypoxia-inducing agents, wherein said one or more hypoxia-inducing agents comprise a stilbene in an amount effective to induce hypoxia in the tumor, wherein said stilbene is cis-3,4',5-trimethoxy-3'-aminostilbene (stilbene 5c) and wherein said hypoxia-activated bioreductive agent is tirapazamine administered before or concurrently with said one or more hypoxia-inducing agents.

2. The method of claim 1, wherein the hypoxia-activated bioreductive agent is administered before the one or more hypoxia-inducing agents are administered.

3. The method of claim 1, wherein the hypoxia-activated bioreductive agent is administered concurrent with the one or more hypoxia-inducing agents.

4. The method of claim 1, wherein said administration is in an amount effective in inducing necrosis of said tumor after 3 days of said administration.

5. The method of claim 1, wherein the one more hypoxia-inducing agents further comprise an anti-angiogenic agent.

6. The method of claim 5, wherein the anti-angiogenic agent is selected from the group consisting of: bevacizumab, sorafenib, sunitinib, aflibercept, IMC-1C11, vatalanib (PTK-87), N-(2,3-dihydro-3,3-dimethyl-1H-indol-6-yl)-2-[(4-pyridinylmethy-1)amino]-3-pyridinecarboxamide (AMG 706), 3-(4-Bromo-2,6-difluoro-benzyloxy)-5-[3-(4-pyrrolidin-1-yl-butyl)-ureido]- -isothiazole-4-carboxylic acid amide (CP-547,632), pazopanib (GW-786034), N-(4-

(3-amino-1H-indazol-4-yl)phenyl)-N'-(2-fluoro-5-methyl-phenyl)urea (ABT-869), and cediranib (AXD-2171).

7. The method of claim 1, wherein said administration of the hypoxia-activated bioreductive agent and the one or more hypoxia-inducing agents synergistically induces necrosis by at least about 5 fold as compared to administering the hypoxia-activated bioreductive agent and/or the one or more hypoxia-inducing agents, alone.

8. The method of claim 1, wherein about 1 mg to about 300 mg of the hypoxia-activated bioreductive agent is administered to the subject.

9. The method of claim 1, wherein about 5 mg to about 200 mg of the hypoxia-activated bioreductive agent is administered to the subject.

* * * * *